United States Patent
Goya et al.

(10) Patent No.: US 8,359,841 B2
(45) Date of Patent: Jan. 29, 2013

(54) EXHAUST PURIFYING APPARATUS FOR AN INTERNAL COMBUSTION ENGINE

(75) Inventors: Yoichiro Goya, Susono (JP); Keiichiro Aoki, Sunto-gun (JP); Nao Murase, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 313 days.

(21) Appl. No.: 12/671,175

(22) PCT Filed: Sep. 9, 2009

(86) PCT No.: PCT/JP2009/066058
§ 371 (c)(1),
(2), (4) Date: Jan. 28, 2010

(87) PCT Pub. No.: WO2010/030034
PCT Pub. Date: Mar. 18, 2010

(65) Prior Publication Data
US 2010/0199636 A1    Aug. 12, 2010

(30) Foreign Application Priority Data
Sep. 10, 2008  (JP) ................................. 2008-232539

(51) Int. Cl.
*F01N 3/00* (2006.01)
(52) U.S. Cl. .......................................... 60/295; 60/301
(58) Field of Classification Search .................... 60/276, 60/286, 295, 301, 303, 285, 297
See application file for complete search history.

(56) References Cited

U.S. PATENT DOCUMENTS

| | | | |
|---|---|---|---|
| 6,017,503 A | 1/2000 | Kato et al. | |
| 6,210,641 B1* | 4/2001 | Yamada et al. | 422/94 |
| 2006/0130461 A1* | 6/2006 | Gabrielsson et al. | 60/286 |
| 2007/0283685 A1 | 12/2007 | Ripper et al. | |
| 2008/0066454 A1* | 3/2008 | Viola | 60/286 |
| 2009/0260987 A1* | 10/2009 | Valdes et al. | 204/424 |
| 2011/0000290 A1* | 1/2011 | Sawada et al. | 73/114.75 |

FOREIGN PATENT DOCUMENTS

| | | |
|---|---|---|
| CN | 101084053 A | 12/2007 |
| DE | 697 25 070 T2 | 7/2004 |

(Continued)

OTHER PUBLICATIONS

Machine Translation of JP 2005-127256 A.*

(Continued)

*Primary Examiner* — Thomas Denion
*Assistant Examiner* — Patrick Maines
(74) *Attorney, Agent, or Firm* — Oliff & Berridge, PLC

(57) ABSTRACT

A present exhaust purifying apparatus comprises a SCR catalyst, a urea-water injector, and a downstream air-fuel ratio sensor (an oxygen concentration sensor having a diffusion resistance layer) disposed at a position downstream of the SCR catalyst. The present apparatus, when a predetermined condition is satisfied, stops injecting the urea-water from the urea-water injector, and obtains an output value of the downstream air-fuel ratio sensor, as a first output value, in that state. The present apparatus obtains an output value of the downstream air-fuel ratio sensor when the urea-water is being injected from the urea-water injector, as a second output value. The present apparatus obtains a concentration of ammonia which flows out from the SCR catalyst based on the difference between the first output value and the second output value.

5 Claims, 15 Drawing Sheets

FOREIGN PATENT DOCUMENTS

| | | |
|---|---|---|
| DE | 10 2004 054 238 A1 | 5/2006 |
| EP | 0 820 799 A2 | 1/1998 |
| JP | A 5-149170 | 6/1993 |
| JP | A 10-33948 | 2/1998 |
| JP | A 11-72473 | 3/1999 |
| JP | A 2000-65782 | 3/2000 |
| JP | A 2001-124730 | 5/2001 |
| JP | A 2003-314256 | 11/2003 |
| JP | A 2004-69547 | 3/2004 |
| JP | 2005127256 A * | 5/2005 |
| JP | A 2005-127256 | 5/2005 |
| JP | A 2005-169331 | 6/2005 |
| JP | 2005233117 A * | 9/2005 |
| JP | A 2005-233117 | 9/2005 |
| JP | 2006274844 A * | 10/2006 |
| JP | A 2008-519932 | 6/2008 |
| KR | 1020070084091 A | 8/2007 |
| WO | WO 2006/051017 A1 | 5/2006 |

OTHER PUBLICATIONS

Machine Translation of JP 2005-233117 A.*
Machine Translation of JP 2006-274844 A.*
Machine Translation of JP 2005-127256 A, Machine Translated on Oct. 24, 2012.*
Machine Translation of JP 2005-233117 A, Machine Translated on Oct. 24, 2012.*
Machine Translation of JP 2006-274844 A, Machine Translated on Oct. 24, 2012.*
International Search Report issued for International Application No. PCT/JP2009/066058 on Nov. 17, 2009 (with translation).

* cited by examiner

Oxygen cell characteristic

EXHAUST PURIFYING APPARATUS FOR AN INTERNAL COMBUSTION ENGINE

TECHNICAL FIELD

The present invention relates to an exhaust purifying apparatus for an internal combustion engine having a SCR catalyst disposed in an exhaust passage.

BACKGROUND ART

A SCR (Selective Catalytic Reduction) catalyst is a catalyst which purifies nitrogen oxides (NOx) by reducing the nitrogen oxides with ammonia ($NH_3$). Especially, the SCR catalyst has started to be used for a diesel engine which emits a comparatively large amount of nitrogen oxides. The SCR catalyst is referred to as "a NOx selective reduction catalyst" or as "an adding ammonia type NOx catalyst".

Reducing nitrogen oxides by the SCR catalyst requires to provide the SCR catalyst with ammonia which serves as a reduction agent for nitrogen oxides. A conventional apparatus provides the SCR catalyst with ammonia itself, or it supplies a water (urea-water, urea aqueous solution) containing urea ($CO(NH_2)_2 = H_2N—CO—NH_2$) to an upstream of the SCR catalyst, instead. The urea changes into ammonia and carbon dioxides on hydrolysis. The ammonia obtained by the hydrolysis reduces the nitrogen oxides in the SCR catalyst. The system where the urea-water is supplied to an upstream of the SCR catalyst is also referred to as "Urea SCR system". The Ministry of Land, Infrastructure, Transport and Tourism of Japan reports that, on its web page dated December 18 of Heisei 15, "a Urea SCR system study group" has been established. Hereinafter, the ammonia or the urea-water, which is added or supplied as described before, is referred to as "an additive agent" or as "a reduction agent".

Meanwhile, when an excessive amount of ammonia is supplied to the SCR catalyst directly, or when an excessive amount of ammonia is supplied to the SCR catalyst by supplying an excessive amount of urea-water in the Urea SCR system, ammonia which can not react with nitrogen oxides in the SCR catalyst is discharged from the SCR catalyst. That is, an ammonia slip occurs. Occurring the ammonia slip means that the additive agent is consumed wastefully. On the other hand, when the supplied additive agent is insufficient for nitrogen oxides, nitrogen oxides are discharged from the SCR catalyst. Therefore, it is important to control an amount of the supplied additive agent (an amount of ammonia or urea-water) appropriately in such a system using the SCR catalyst.

Accordingly, one of conventional apparatuses comprises an upstream NOx sensor and a downstream NOx sensor, disposed at a position upstream of and at a position downstream of the SCR catalyst, respectively. The conventional apparatus controls "an amount of urea-water to be supplied" based on a concentration of nitrogen oxides detected by those sensors (refer to, for example, Japanese Patent Application Laid-Open (kokai) No. 2005-127256).

SUMMARY OF THE INVENTION

However, the conventional apparatus has a problem that it uses two NOx sensors, each of which is expensive, and thus, the cost for the whole system is high. Therefore, one of objects of the present invention is to provide "an exhaust purifying apparatus using a SCR catalyst" which is more inexpensive, by enabling "an inexpensive downstream air-fuel ratio sensor" in place of "the expensive downstream NOx sensor" to be used for controlling an amount of the additive agent.

The exhaust purifying apparatus according to the present invention comprises a SCR catalyst (a SCR catalytic converter), a downstream air-fuel ratio sensor, additive agent supplying means, first output value obtaining means, second output value obtaining means, ammonia-amount-relating-value obtaining means, and additive agent amount control means. An internal combustion engine to which the exhaust purifying apparatus is applied is an engine (e.g., a diesel engine) which can be operated with a lean air-fuel mixture, whose air-fuel ratio is in lean side compared to stoichiometric air-fuel ratio. Thus, an exhaust gas discharged from the engine typically contains oxygen and nitrogen oxides.

The SCR catalyst is disposed in an exhaust passage of the internal combustion engine. As described above, the SCR catalyst reduces nitrogen oxides contained in the exhaust gas discharged from the internal combustion engine by ammonia. This allows the SCR catalyst to purify the nitrogen oxides contained in the exhaust gas.

The downstream air-fuel ratio sensor is disposed "at a position downstream of said SCR catalyst in the exhaust passage (in the exhaust passage at the downstream of the SCR catalyst). The downstream air-fuel ratio sensor includes a solid electrolyte layer, an exhaust gas side electrode layer, an atmospheric air side electrode layer exposed in a space to which atmosphere is introduced, and a diffusion resistance layer. The exhaust gas side electrode layer and the atmospheric air side electrode layer are formed on both surfaces of the solid electrolyte layer, respectively, so as to oppose to each other to sandwich the solid electrolyte layer. The exhaust gas side electrode layer is covered by the diffusion resistance layer. The diffusion resistance layer is arranged/configured in such a manner that a gas which is sensed (a gas to be detected) contacts with an outer surface of the diffusion resistance layer. The downstream air-fuel ratio sensor outputs an output value varying in accordance with "a concentration of oxygen at the exhaust gas side electrode layer" of "the gas which reaches the exhaust gas side electrode layer after passing through the diffusion resistance layer". That is, the downstream air-fuel ratio sensor is "a well-known air-fuel ratio sensor" which detects an air-fuel ratio of a gas, by detecting a concentration of oxygen. It should be noted that the gas which has reached the outer surface of the diffusion resistance layer is referred to as "a downstream gas to be detected", for convenience, hereinafter.

The additive agent supplying means is configured so as to supply an additive agent which may be "urea-water or ammonia" at a position upstream of the SCR catalyst in the exhaust passage in response to an instruction. When the urea-water is supplied, the urea is hydrolyzed so that ammonia is formed. Thus, the additive agent supplying means is "ammonia supplying means" for supplying ammonia to the SCR catalyst.

The first output value obtaining means is configured so as to obtain "a first output value" which is "a value varying in accordance with (depending on) a concentration of oxygen" contained in "the exhaust gas which is in a state where nitrogen oxides contained in the exhaust gas have not been purified by the SCR catalyst". In other words, the first output value is a value varying depending on a concentration of oxygen of "a gas upstream of the SCR catalyst in the exhaust passage", or depending on a concentration of oxygen of "a gas which has passed through the SCR catalyst" which is in a state where the SCR catalyst can not reduce the nitrogen oxides because the additive agent is not supplied to the SCR catalyst. As described later, the first output value can be obtained based on either "the output value of the downstream air-fuel ratio sensor" or "an output value of an upstream air-fuel ratio sensor".

The second output value obtaining means is configured so as to obtain "a second output value" which is a value based on "the output value of the downstream air-fuel ratio sensor" when (or which is in a state where) the additive agent supplying means is supplying the additive agent (into the position upstream of the SCR catalyst in the exhaust passage). "The value based on the output value of the downstream air-fuel ratio sensor" may be "the output value of the downstream air-fuel ratio sensor itself" or "a value obtained by correcting the output value of the downstream air-fuel ratio sensor" as described later.

The ammonia-amount-relating-value obtaining means obtains a value which relates to "an amount of ammonia which flows out from the SCR catalyst" (that is, the ammonia-amount-relating-value obtaining means obtains the value referred to as an ammonia-amount-relating-value), based on a difference between the first output value and the second output value. For example, the ammonia-amount-relating-value is a value which represents a concentration of ammonia, or is a value which shows existence or nonexistence of ammonia (whether or not a concentration of ammonia is 0), etc. "The difference between the first output value and the second output value" may be a difference between the first output value and the second output value itself, or may include a ratio of the first output value to the second output value or vice versa, etc. In other words, "the difference between the first output value and the second output value" is a value based on a comparison between the first output value and the second output value.

The additive agent amount control means determines "an amount of the additive agent to be supplied" based on "the obtained ammonia-amount-relating-value". Further, the additive agent amount control means is configured so as to send to the additive agent supplying means an instruction to supply the additive agent of the determined amount (an instruction to make the additive agent supplying means supply the determined amount of the additive agent at the position upstream of the SCR catalyst in the exhaust passage).

The second output value is "a value based on the output value of the downstream air-fuel ratio sensor" when the additive agent is being supplied. That is, the second output value is "a value based on the output value of the downstream air-fuel ratio sensor" when "the urea-water which is a source for ammonia" or "ammonia itself" is supplied into the exhaust passage, and thereby ammonia is supplied to the SCR catalyst.

At this time, if an amount of the additive agent is excessive for "the nitrogen oxides to be reduced or purified in the SCR catalyst" (in other words, ammonia of an amount greater than "an amount of ammonia required to reduce the nitrogen oxides in the exhaust gas" is supplied to the SCR catalyst), a gas containing the excessive ammonia is flowed out from the SCR catalyst. The gas reaches the outer surface of the diffusion resistance layer of the downstream air-fuel ratio sensor. Therefore, the downstream gas to be detected contains the oxygen (oxygen molecules) and the ammonia (ammonia molecules). The oxygen and the ammonia move in the diffusion resistance layer by diffusion.

Meanwhile, a diameter of an oxygen molecule ($O_2$) is greater than a diameter of an ammonia molecule ($NH_3$). Typically, the diffusion resistance layer is a porous layer having "ceramic grains" and "fine pores formed between or among the ceramic grains". Thus, molecules of gas pass through the fine pores with colliding with the ceramic grains. Therefore, diffusion speed of an oxygen molecule in the diffusion resistance layer is lower than diffusion speed of an ammonia molecule in the diffusion resistance layer. In other words, "a sum (an integrated value) of moving distance required for the oxygen molecule to pass through the diffusion resistance layer is greater than a sum (an integrated value) of moving distance required for the ammonia molecule to pass through the diffusion resistance layer. Accordingly, if the downstream gas to be detected contains ammonia, the ammonia passes through the diffusion resistance layer and reaches the exhaust gas side electrode layer more preferentially than the oxygen. Furthermore, the ammonia combines with the oxygen at the exhaust gas side electrode layer (that is, the ammonia is oxidized and the oxygen is consumed).

As a result, the output value of the downstream air-fuel ratio sensor, when a concentration of oxygen of the downstream gas to be detected is a given concentration and the downstream gas to be detected contains ammonia, becomes a value showing that "the downstream gas to be detected is a gas whose concentration of oxygen is smaller (richer gas)", as compared with the output value of the downstream air-fuel ratio sensor when a concentration of oxygen of the downstream gas to be detected is the given concentration and the downstream gas to be detected contains no ammonia.

That is, even when the concentration of the oxygen contained in the downstream gas to be detected is constant, the second output value based on the output of the downstream air-fuel ratio sensor becomes a value which shows that the concentration of oxygen contained in the downstream gas is smaller, as the concentration of ammonia contained in the downstream gas to be detected is higher.

On the other hand, the first output value is a value varying in accordance with "the concentration of oxygen contained in the exhaust gas which is in a state where the nitrogen oxides has not been purified". Therefore, the first output value becomes a value corresponding to the second output value when the downstream gas to be detected contains no ammonia.

Accordingly, the difference between the first output value and the second output value becomes a value relating to the amount of ammonia flowing out from the SCR catalyst (an ammonia-amount-relating-value, for example, a value varying depending on the concentration of ammonia). In view of the above, the ammonia-amount-relating-value obtaining means obtains the ammonia-amount-relating-value based on the difference between the first output value and the second output value.

Further, the additive agent amount control means determines "an amount of the additive agent to be supplied" based on said ammonia-amount-relating-value. For example, when the ammonia-amount-relating-value shows that "a large amount of ammonia is flowed out from the SCR catalyst", "the amount of the additive agent to be supplied" is decreased. To the contrary, when the ammonia-amount-relating-value shows that "the ammonia is not flowed out from the SCR catalyst", "the amount of the additive agent to be supplied" is increased. Thereafter, the additive agent amount control means sends to the additive agent supplying means an instruction to supply the determined amount of the additive agent.

As described above, the exhaust purifying apparatus according to the present invention comprises the air-fuel ratio sensor downstream of the SCR catalyst instead of the NOx sensor, and can control "the supply amount of the additive agent" appropriately by utilizing the air-fuel ratio sensor (the downstream air-fuel ratio sensor). At present, a cost of the air-fuel ratio sensor is one-third of a cost of the NOx sensor. Thus, the present invention can provide the exhaust purifying apparatus which is very inexpensive.

In one of aspects of the present exhaust purifying apparatus, the first output value obtaining means is configured so as to obtain, as "the first output value", "the output value of the downstream air-fuel ratio sensor" when "the additive agent supplying means does not supply (or is not supplying) the additive agent";

the second output value obtaining means is configured so as to obtain, as "the second output value", "the output value of the downstream air-fuel ratio sensor" when "the additive agent supplying means supplies (or is supplying) the additive agent"; and the additive agent amount control means is configured so as to send "an instruction to stop supplying the additive agent" to the additive agent supplying means, in order to "make the first output value obtaining means obtain the first output value", when a first predetermined condition (a predetermined first condition) is satisfied.

The first predetermined condition may be, for example, a condition which is satisfied every time a predetermined time period elapses, or a condition which is satisfied when an operating condition of the engine (e.g., the engine load which is represented by an operation amount of an accelerator pedal) has changed by a predetermined amount or more.

This aspect can obtain "the first output value and the second output value" by using "the downstream air-fuel ratio sensor only". Thus, for example, it is not necessary to dispose "an upstream air-fuel ratio sensor to obtain the first output value" at a position upstream of the SCR catalyst in the exhaust passage. Accordingly, the exhaust purifying apparatus which is more inexpensive can be provided.

Further, in another aspect of the exhaust purifying apparatus, the first output value obtaining means is configured so as to include an upstream air-fuel ratio sensor which is disposed at the position upstream of the SCR catalyst in the exhaust passage and so as to obtain, as "the first output value", "a value based on the output value of the upstream air-fuel ratio sensor". The value based on the output value of the upstream air-fuel ratio sensor may be "the output value of the upstream air-fuel ratio sensor itself" or "a value obtained by correcting the output value of the upstream air-fuel ratio sensor", as described later.

In this case, the upstream air-fuel ratio sensor has a structure similar to the downstream air-fuel ratio sensor. That is, the upstream air-fuel ratio sensor includes a solid electrolyte layer, an exhaust gas side electrode layer, an atmospheric air side electrode layer exposed in a space to which atmosphere is introduced, and a diffusion resistance layer. The exhaust gas side electrode layer and the atmospheric air side electrode layer are formed on both surfaces of the solid electrolyte layer, respectively, so as to oppose to each other to sandwich the solid electrolyte layer. The exhaust gas side electrode layer is covered by the diffusion resistance layer. The diffusion resistance layer is arranged/configured in such a manner that a gas which is sensed (a gas to be detected) contacts with an outer surface of the diffusion resistance layer. In addition, the upstream air-fuel ratio sensor outputs an output value varying in accordance with "a concentration of oxygen at the exhaust gas side electrode layer" of "the gas which reaches the exhaust gas side electrode layer after reaching the outer surface of the diffusion resistance layer and passing through the diffusion resistance layer".

The exhaust gas in "a state where the nitrogen oxides contained in the exhaust gas has not been purified by the SCR catalyst" arrives always at the upstream air-fuel ratio sensor (the outer surface of the diffusion resistance layer of the upstream air-fuel ratio sensor). Thus, it is not necessary to stop supplying the additive agent in order to obtain the first output value, if "a value based on the output value of the upstream air-fuel ratio sensor" is obtained as "the first value". Accordingly, this aspect can always supply the additive agent to the SCR catalyst. Thus, this aspect can control the amount of the additive agent appropriately while purifying the nitrogen oxides.

Furthermore, in the exhaust purifying apparatus of this aspect, the first output value obtaining means is configured so as to obtain "the output value of the upstream air-fuel ratio sensor" as "the first output value".

The second output value obtaining means is configured so as to obtain "an output value for an upstream side correction" which is "the output value of the upstream air-fuel ratio sensor" at "a given timing at which the additive agent supplying means does not supply (is not supplying) the additive agent", and so as to obtain "an output value for an downstream side correction" which is "the output value of the downstream air-fuel ratio sensor at the given timing".

Furthermore, the second output value obtaining means is configured so as to correct, based on "the output value for an upstream side correction and the output value for an downstream side correction", "the output value of the downstream air-fuel ratio sensor" when "the additive agent supplying means supplies (is supplying) the additive agent", in order to obtain "the corrected value" as "the second output value".

In addition, the additive agent amount control means is configured so as to send, to the additive agent supplying means, "an instruction to stop supplying the additive agent", in order to make "the second output value obtaining means" obtain "the output value for an upstream side correction and the output value for an downstream side correction", when a second predetermined condition (a predetermined second condition) is satisfied.

Generally, "output values of air-fuel ratio sensors", such as the output value of the upstream air-fuel ratio sensor and the output value of the downstream air-fuel ratio sensor, for "a given concentration of oxygen of the gas to be detected" may vary due to "individual deviations of output characteristic and their temperatures". Accordingly, even when the ammonia does not flow our from the SCR catalyst, "the output value of the downstream air-fuel ratio sensor" is not necessary equal to "the output value of the upstream air-fuel ratio sensor". The result is that, the obtained ammonia-amount-relating-value may not be accurate, when the output value of the upstream air-fuel ratio sensor itself is obtained as the first output value, the output value of the downstream air-fuel ratio sensor itself is obtained as the second output value, and "the ammonia-amount-relating-value" is simply obtained based on the difference between the first output value and the second output value.

The exhaust purifying apparatus of the above aspect, in order to avoid that an accuracy of the ammonia-amount-relating-value is degraded, obtains "the output value of the downstream air-fuel ratio sensor" at "the given timing at which the additive agent supplying means does not supply (is not supplying) the additive agent" as "the output value for an downstream side correction" and obtains "the output value of the upstream air-fuel ratio sensor" at "the given timing" as "the output value for an upstream side correction". At the given timing, it is assumed that a concentration of oxygen contained in the exhaust gas at the position upstream of the SCR catalyst is the same as a concentration of oxygen contained in the exhaust gas at the position downstream of the SCR catalyst, since the ammonia is not supplied to the SCR catalyst. Accordingly, if the output characteristic of the upstream air-fuel ratio sensor is the same as the output characteristic of the downstream air-fuel ratio sensor, the output value for an upstream side correction and the output value for a downstream side correction should be equal to each other. In other words, a difference between the output value for an upstream side correction and the output value for a downstream side correction varies depending on the difference in output characteristic between the upstream air-fuel ratio sensor and the downstream air-fuel ratio sensor.

In view of the above, the exhaust purifying apparatus of the above aspect obtains, as the second output value, a corrected value obtained by correcting, based on "the output value for an upstream side correction and the output value for an downstream side correction (e.g., a ratio of these output values)", "the output value of the downstream air-fuel ratio sensor" when "the additive agent supplying means supplies (is supplying) the additive agent".

As a result, the second output value becomes a value which is obtained by the downstream air-fuel ratio sensor as if which has the same output characteristic as the upstream air-fuel ratio sensor. As a result, the difference between the first output value and the second output value becomes a value obtained when the difference in output characteristic between the upstream air-fuel ratio sensor and the downstream air-fuel ratio sensor is compensated. Accordingly, it is possible to avoid that the accuracy of "the ammonia-amount-relating-value" which is obtained based on the first output value and the second output value is degraded.

Meanwhile, in another aspect of the exhaust purifying apparatus, the second output value obtaining means is configured so as to obtain, "as the second output value", "the output value of the downstream air-fuel ratio sensor" when "the additive agent supplying means supplies (is supplying) the additive agent".

Further, the first output value obtaining means is configured so as to obtain "an output value for a upstream side correction" which is "the output value of the upstream air-fuel ratio sensor" at "a given timing at which the additive agent supplying means does not supply (is not supplying) the additive agent", and so as to obtain "an output value for a downstream side correction which is the output value of the downstream air-fuel ratio sensor" at the given timing.

Furthermore, the first output value obtaining means is configured so as to obtain, as "the first output value", a corrected value obtained by correcting, based on "the output value for an upstream side correction and the output value for an downstream side correction", "the output value of the upstream air-fuel ratio sensor" when "the additive agent supplying means supplies (is supplying) the additive agent".

The additive agent amount control means is configured so as to send "an instruction to stop supplying the additive agent" to the additive agent supplying means, in order to make "the first output value obtaining means" obtain "the output value for an upstream side correction and the output value for an downstream side correction", when a third predetermined condition (a predetermined third condition) is satisfied.

In this case as well, as described above, the difference between the output value for an upstream side correction and the output value for a downstream side correction varies depending on the difference in output characteristic between the upstream air-fuel ratio sensor and the downstream air-fuel ratio sensor. Accordingly, the corrected value obtained by correcting "the output value of the upstream air-fuel ratio sensor when the additive agent is supplied", with/based on the "the output value for an upstream side correction and the output value for an downstream side correction (e.g., a ratio of these output values)", becomes a value which is obtained by the air-fuel ratio sensor as if which has the same output characteristic as the downstream air-fuel ratio sensor. As a result, the difference between the first output value and the second output value becomes a value obtained when the difference in output characteristic between the upstream air-fuel ratio sensor and the downstream air-fuel ratio sensor is compensated. Accordingly, it is possible to avoid that the accuracy of "the ammonia-amount-relating-value" which is obtained based on the first output value and the second output value is degraded.

Here, a first diffusion distance L1 is defined to be a sum of distance which the ammonia molecule needs/takes when it moves from an outer surface of the diffusion resistance layer to the exhaust gas side electrode layer while passing through the diffusion resistance layer of the downstream air-fuel ratio sensor, a second diffusion distance L2 is a sum of distance which the oxygen molecule needs/takes when it moves from the outer surface of the diffusion resistance layer to the exhaust gas side electrode layer while passing through the diffusion resistance layer of the downstream air-fuel ratio sensor, a third diffusion distance L3 is defined to be a sum of distance which the ammonia molecule needs/takes when it moves from the outer surface of the diffusion resistance layer to the exhaust gas side electrode layer while passing through the diffusion resistance layer of the upstream air-fuel ratio sensor, and a fourth diffusion distance L4 is defined to be a sum of distance which the oxygen molecule needs/takes when it moves from the outer surface of the diffusion resistance layer to the exhaust gas side electrode layer while passing through the diffusion resistance layer of the upstream air-fuel ratio sensor.

Under these definitions, it is preferable that a ratio (L2/L1) of the second diffusion distance L2 to the first diffusion distance L1 be greater than a ratio (L4/L3) of the fourth diffusion distance L4 to the third diffusion distance L3.

This type of the downstream air-fuel ratio sensor can be easily manufactured, for example, as follows.

(1) A mean diameter of the pores of the diffusion resistance layer of the downstream air-fuel ratio sensor is formed/configured to have a diameter such that ammonia molecules can more easily pass through the diffusion resistance layer (than oxygen molecules), and oxygen molecules can more hardly pass through the diffusion resistance layer, compared with the diffusion resistance layer of the upstream air-fuel ratio sensor; and/or (2) A thickness of the diffusion resistance layer of the downstream air-fuel ratio sensor is formed to be greater than a thickness of the diffusion resistance layer of the upstream air-fuel ratio sensor.

This can allow the downstream air-fuel ratio sensor to be much more sensitive to ammonia (i.e., the difference between the first output value and the second output value is increased). As a result, it is possible to obtain more accurate ammonia-amount-relating-value.

DESCRIPTION OF THE EMBODIMENT

Embodiments of an exhaust purifying apparatus for an internal combustion engine according to the present invention will next be described with reference to the drawings.

First Embodiment

Construction

Figure 1:
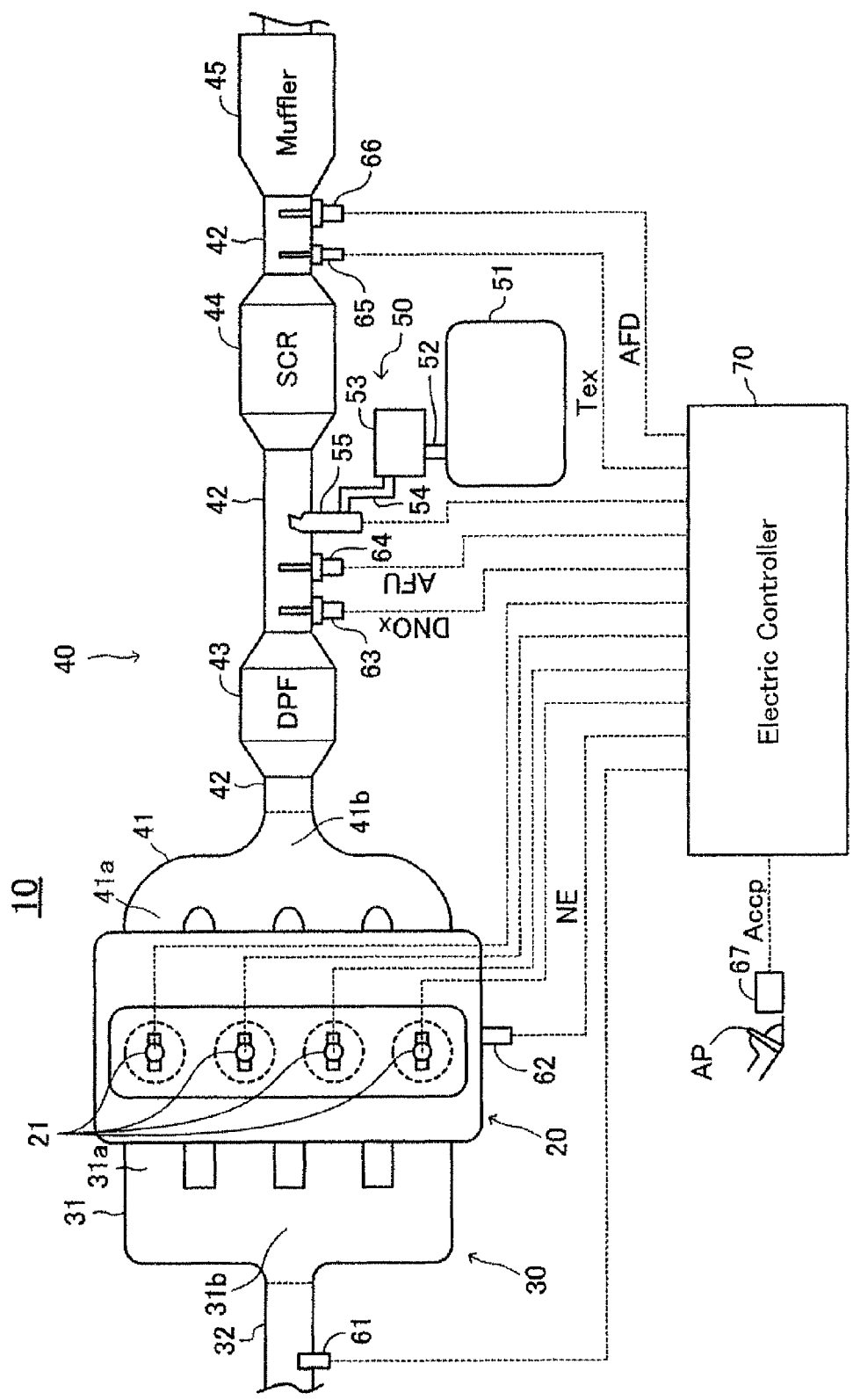
FIG. 1 is a schematic diagram of an internal combustion engine to which an exhaust purifying apparatus according to a first embodiment of the present invention (a first exhaust purifying apparatus) is applied.

FIG. 1 shows a schematic configuration of an internal combustion engine 10 to which an exhaust purifying apparatus (hereinafter, referred simply to as "a first exhaust purifying apparatus") according to a first embodiment of the present invention is applied. The engine 10 is an in-line four cylinder diesel engine. As described below, a diesel engine is operated with a lean air-fuel mixture. Accordingly, in the most case, an exhaust gas discharged from the engine 10 contains oxygen.

The engine 10 comprises an engine main body 20, an intake system 30, an exhaust system 40, and a urea-water supplying device (an additive agent supplying device) 50. Further, the first exhaust purifying apparatus includes an electric controller 70.

The engine main body 20 comprises a crank case section, a cylinder block section, and a cylinder head section. The engine main body 20 has a plurality of (four of) combustion chambers (cylinders), each of which is defined by a head of a piston, a cylinder wall surface, and a lower surface of the cylinder head section. Each of fuel injectors 21 is disposed at the top of each of the combustion chambers. "A high pressure fuel" is supplied to each of the fuel injectors 21 from "a fuel pump (not shown) which is communicated with a fuel tank (not shown)". Each of the fuel injectors 21 is opened in response to an instruction signal from the electric controller 70 to thereby inject the high pressure fuel into each of the combustion chambers.

The intake system 30 includes an intake manifold 31 and an intake pipe 32.

The intake manifold 31 comprises a plurality of branch portions 31a and a merged portion 31b into which the branch portions 31a merge. Each of the plurality of branch portions 31a is connected to each of the combustion chambers through each of intake ports.

The intake pipe 32 is connected to the merged portion 31b of the intake manifold 31.

The exhaust system 40 includes an exhaust manifold 41, an exhaust pipe 42, a diesel particulate filter (DPF) 43, a SCR catalyst (SCR catalytic converter) 44, and a muffler 45.

The exhaust manifold 41 comprises a plurality of branch portions 41a and a merged portion 41b into which the plurality of branch portions 41a merge. Each of the plurality of branch portions 41a is connected to each of the combustion chambers through each of exhaust ports.

The exhaust pipe 42 is connected to the merged portion 41b of the exhaust manifold 41.

The DPF 43 is disposed in the exhaust pipe 42 (exhaust passage). The DPF 43 comprises "a plurality of passages" formed by "dividing walls made of porous material (e.g., cordierite which is one kind of ceramics)". The DPF 43 collects particulates contained in "an exhaust gas passing through the dividing walls" at surfaces of fine holes of the dividing walls. That is, the DPF 43 is a honeycomb-structure wall-flow type particulate filter.

The SCR catalyst 44 is disposed at "a position downstream of the DPF 43" of the exhaust pipe 42 (exhaust passage). The SCR catalyst 44 is a catalytic unit which purifies nitrogen oxides (NOx) by reducing the nitrogen oxides (NOx) with ammonia (NH$_3$). In the present example, the SCR 44 is the catalytic unit/converter which supports zeolitic catalyst on a support made of ceramics. The SCR catalyst may be a vanadium series catalyst.

When nitrogen oxides and ammonia are supplied into the SCR 44, chemical reactions occur as shown by formulas of (1)-(3) described below, and nitrogen oxides are therefore reduced/purified. The reaction described by the formula (3) below occurs most preferentially.

$$4NO+4NH_3+O_2 \rightarrow 4N_2+6H_2O \qquad (1)$$

$$6NO_2+8NH_3 \rightarrow 7N_2+12H_2O \qquad (2)$$

$$NO+NO_2+2NH_3 \rightarrow 2N_2+3H_2O \qquad (3)$$

The muffler 45 is disposed at "a position downstream of the SCR catalyst 44" of the exhaust pipe 42 (exhaust passage).

The urea-water supplying device (an additive agent supplying device) 50 composes/constitutes additive agent supplying means for supplying urea-water in response to an instruction signal at/to the position upstream of the SCR catalyst 44 of the exhaust pipe 42 (exhaust passage). The urea-water supplying device 50 may be replaced by an ammonia supplying device for supplying ammonia in place of the urea-water. "The urea-water or the ammonia" may be referred to as "an additive agent (additive agent for the SCR catalyst)" in the present specification.

The urea-water supplying device 50 includes a urea-water tank 51, a first connection pipe 52, a urea-water pressurizing device 53, a second connection pipe 54, and urea-water injector 55.

The urea-water tank 51 is configured in such a manner that it stores the urea-water (urea aqueous solution) having a predetermined concentration.

The first connection pipe 52 connects the urea-water tank 51 with the urea-water pressurizing device 53.

The urea-water pressurizing device 53 is configured in such a manner that it pipes up the urea-water in the urea-water tank 51 through the first connection pipe 52 (it pressurizes the urea-water up to a predetermined pressure), and supplies the urea-water to the second connection pipe 54.

The second connection pipe 54 connects the urea-water pressurizing device 53 with the urea-water injector 55.

The urea-water injector 55 opens for a predetermined time period in response to an instruction signal (a urea-water injection signal) from the electric controller 70, to thereby inject (supply) a predetermined amount of "the urea water supplied through the second connection pipe 54" at or to "the position upstream of the SCR catalyst 44 (and downstream of the DPF 43) in the exhaust passage 42".

Further, the first exhaust purifying apparatus comprises an air flowmeter 61, an engine rotational speed sensor 62, a NOx sensor 63, an upstream air-fuel ratio sensor 64, an exhaust gas temperature sensor 65, a downstream air-fuel ratio sensor 66, and an accelerator opening sensor 67.

The air flowmeter 61 is disposed in the intake pipe 32 (intake passage). The air flowmeter 61 outputs a signal Ga representing "an amount of intake air", which is a mass flow rate of the air passing through the intake passage (an amount of air per unit time).

The engine rotational speed sensor 62 detects a rotational speed of the engine 10 so as to output a signal representing the engine rotational speed NE.

The NOx sensor 63 is disposed at "a position downstream of the DPF 43" of the exhaust pipe 42 (exhaust passage) and at "the position upstream of the urea-water injector 55". Accordingly, the NOx sensor 63 is disposed at a position upstream of the SCR catalyst 44 of the exhaust pipe 42. The NOx sensor 63 detects a concentration of nitrogen oxides contained in the exhaust gas which reaches the NOx sensor 36 so as to output a signal DNOx representing the concentration of the nitrogen oxides. That is, the NOx sensor 63 is configured in such a manner that it detects the concentration of nitrogen oxides DNOx of "an exhaust gas which is discharged from the combustion chambers of the engine main body 20 and has not yet passed through the SCR catalyst 44 (i.e., the gas which is in a condition before the nitrogen oxides has been purified)".

The upstream air-fuel ratio sensor 64 is disposed at "the position downstream of the DPF 43" of the exhaust pipe 42 (exhaust passage) and at "the position upstream of the urea-water injector 55". Accordingly, the upstream air-fuel ratio sensor 64 is disposed at the position upstream of the SCR catalyst 44 of the exhaust pipe 42.

The upstream air-fuel ratio sensor 64 is "a wide range air-fuel ratio sensor of a limiting current type having a diffusion resistance layer" described in, for example, Japanese Patent Application Laid-Open (kokai) No. Hei 11-72473, Japanese Patent Application Laid-Open No. 2000-65782, and Japanese Patent Application Laid-Open No. 2004-69547, etc. The upstream air-fuel ratio sensor 64 detects a concentration of oxygen contained in the exhaust gas which reaches the upstream air-fuel ratio sensor 64, so as to generate an output value AFU representing the concentration of oxygen. The output value AFU can be said to be "an air-fuel ratio of the exhaust gas reaching the upstream air-fuel ratio sensor 64". That is, the upstream air-fuel ratio sensor 64 is configured so as to output the output value AFU which varies according to the concentration of oxygen of "the exhaust gas which is discharged from the combustion chambers of the engine main body 20 and which has not yet passed through the SCR catalyst 44 (i.e., the exhaust gas which is in a condition where nitrogen oxides has not been purified)".

Figure 2:
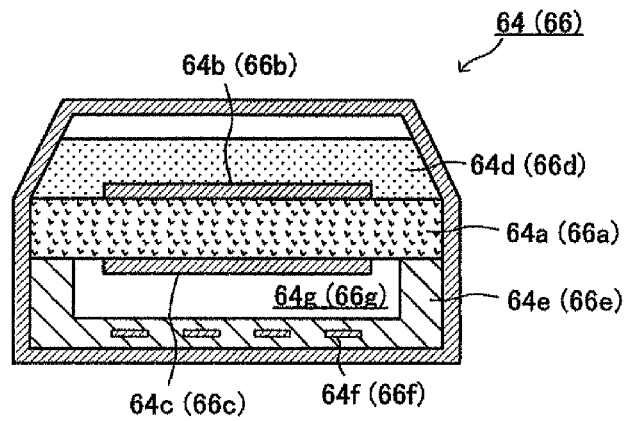
FIG. 2 is a sectional view of an upstream air-fuel ratio sensor shown in FIG. 1.

Specifically, as shown in FIG. 2, the upstream air-fuel ratio sensor 64 includes a solid electrolyte layer 64a, an exhaust gas side electrode layer 64b, an atmospheric air side electrode layer 64c, a diffusion resistance layer 64d, a septum wall section 64e, and a heater 64f.

The solid electrolyte layer 64a is a sintered body made of an oxide having oxide ion conductivity. In the present example, the solid electrolyte layer 64a is "a stabilized zirconia element" made of CaO—ZrO$_2$ (zirconia) solid solution, where the CaO serves as a stabilization agent. The solid electrolyte layer 64a shows a well known "oxygen cell characteristic" and a well known "oxygen pump characteristic", when a temperature of the solid electrolyte layer 64a is higher than an activation temperature. These characteristics are ones that should be exhibited when the upstream air-fuel ratio sensor 64 outputs a value in response to a concentration of oxygen in the exhaust gas (or an air-fuel ratio of the exhaust gas). The oxygen cell characteristic is a characteristic that the sensor generates an electro motive force by having oxygen ions pass from an area of higher concentration of oxygen to an area of lower concentration of oxygen. The oxygen pump characteristic is a characteristic that, when a potential difference is supplied between both sides of the solid electrolyte layer 64a, the sensor makes "oxygen ions" move from the negative electrode to the positive electrode, where an amount of moved oxygen ions varies in accordance with the potential difference between a negative electrode (lower potential electrode) and a positive electrode (higher potential electrode).

The exhaust gas side electrode layer 64b is made of a precious metal having a high catalytic activity such as Platinum (Pt). The exhaust gas side electrode layer 64b is formed on one of surfaces of the solid electrolyte layer 64a. The exhaust gas side electrode layer 64b is formed by chemical plating etc. in such a manner that it has an excellent infiltration (i.e., it is porous). "The exhaust gas which is discharged from the combustion chambers of the engine main body 20 and has not yet passed through the SCR catalyst 44" reaches the exhaust gas side electrode layer 64b. This exhaust gas may be referred to as "an upstream-side gas to be detected".

The atmospheric air side electrode layer 64c is made of a precious metal having a high catalytic activity such as Platinum (Pt). The atmospheric air side electrode layer 64c is formed on the other one of surfaces of the solid electrolyte layer 64a so as to oppose to the exhaust gas side electrode layer 64b to sandwich the solid electrolyte layer 64a. The atmospheric air side electrode layer 64c is formed by chemical plating etc. in such a manner that it has an excellent infiltration (i.e., it is porous).

The diffusion resistance layer (diffusion controlling layer) 64d is made of a porous ceramic (thermally-resistant inorganic substance). That is, the diffusion resistance layer 64d is a porous layer having "ceramic grains" and "fine pores formed among the ceramic grains". Molecules of gas pass through the fine pores with (while) colliding with the ceramic grains. The diffusion resistance layer 64d is formed by, for example" a plasma spraying, etc. so as to cover the outer surface of the exhaust gas side electrode layer 64b.

The septum wall section 64e is made of an alumina ceramics which is dense and does not allow gas to pass through. The septum wall section 64e is formed so as to provide "an air chamber 64g" which is "a space which accommodates/houses the atmospheric air side electrode layer 64c". Thus, the atmospheric air side electrode layer 64c is exposed in the air chamber 64g which is a space into which air (atmosphere) is introduced. Accordingly, a concentration of oxygen (an oxygen partial pressure) at the atmospheric air side electrode layer 64c is equal to an concentration of oxygen in the air (an oxygen partial pressure of the air).

The heater 64f is buried in the septum wall section 64e. The heater 64f, when energized, generates heat so as to heat the solid electrolyte layer 64a.

Figure 3:
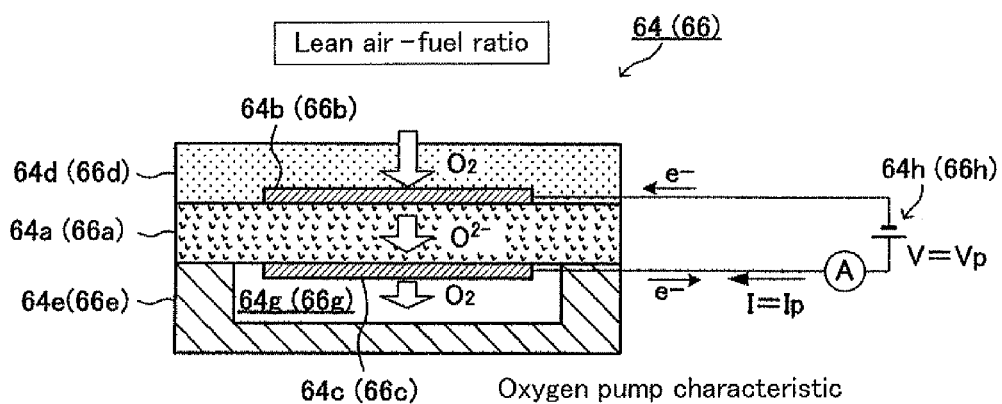
FIG. 3 is a drawing for explaining a principle of detecting a concentration of oxygen by the upstream air-fuel ratio sensor shown in FIG. 1.

As shown in FIG. 3, the upstream air-fuel ratio sensor 64 utilizes an electric power supply 64h. The electric power supply 64h applies a voltage V so that the atmospheric air side electrode layer 64c has high potential and the exhaust gas side electrode layer 64b has low potential.

As shown in FIG. 3, the upstream air-fuel ratio sensor 64 outputs the output value AFU according to "the concentration of oxygen of the upstream-side gas to be detected (i.e., an air-fuel ratio of the upstream-side gas to be detected)" by utilizing the above mentioned oxygen pump characteristic, when the air-fuel ratio of the upstream-side gas to be detected is a lean-side air-fuel ratio leaner than the stoichiometric air-fuel ratio. Specifically, when the air-fuel ratio of the upstream-side gas to be detected is the lean-side air-fuel ratio leaner than the stoichiometric air-fuel ratio, a large amount of "oxygen molecules which have reached an outer surface of the diffusion resistance layer 64d" contained in the gas reach the exhaust gas side electrode layer 64b through the diffusion resistance layer 64d. The oxygen molecules receive electrons at the exhaust gas side electrode layer 64b so as to become oxygen ions. The oxygen ions pass through the solid electrolyte layer 64a, and become oxygen molecules by releasing the electrons. As a result, an electrical current I flows from a positive electrode of the electric power supply 64h to a negative electrode of the electric power supply 64h through the atmospheric air side electrode layer 64c, the solid electrolyte layer 64a, and the exhaust gas side electrode layer 64b.

Figure 4:
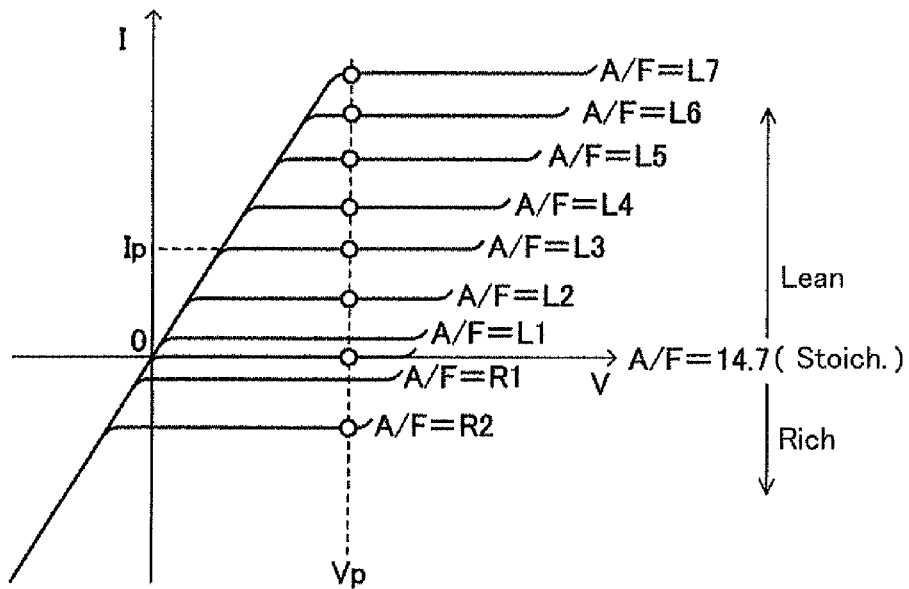
FIG. 4 is a graph showing "a relationship between a voltage supplied to the upstream air-fuel ratio sensor and a limiting current value (an output value of the upstream air-fuel ratio sensor)" for various concentrations of oxygen (air-fuel ratios)

The magnitude of the electrical current I varies, when the magnitude of the voltage V is set to be greater than a predetermined voltage Vp, in accordance with an amount of "the oxygen molecules that are contained in the upstream gas to be detected and that reach the exhaust gas side electrode layer 64b after passing through the diffusion resistance layer 64d by diffusion" (i.e., in accordance with a concentration or a partial pressure of oxygen at the exhaust gas side electrode layer 64b). The electrical current I, as shown in FIG. 4, does not vary even when the voltage V is set to be greater than the predetermined voltage Vp. The electrical current I is therefore referred to as a limiting current Ip. The upstream air-fuel ratio sensor 64 outputs the output value AFU which is proportional to the limiting current Ip. That is, the upstream air-fuel ratio sensor 64 is configured in such a manner that it outputs the output value AFU which varies in accordance with "the concentration (or the partial pressure) of oxygen at the exhaust gas side electrode layer 64b" of the gas which has reached the exhaust gas side electrode layer 64b after passing through the diffusion resistance layer 64d.

Figure 5:
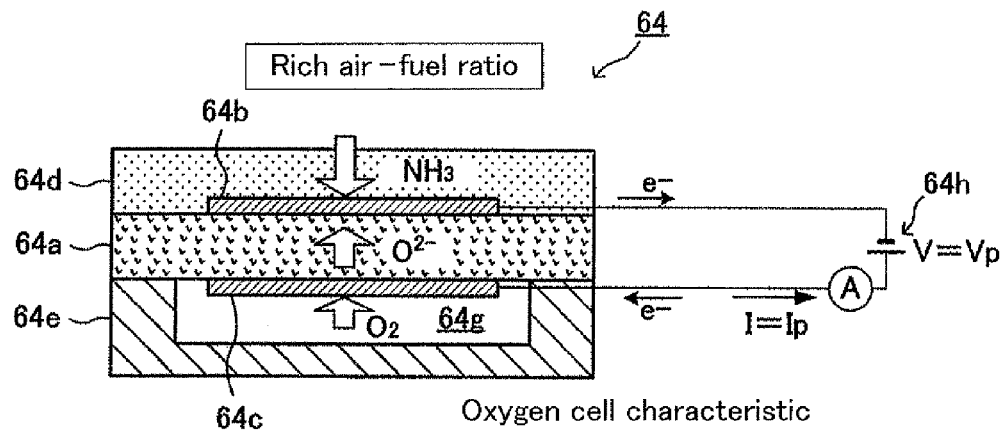
FIG. 5 is a drawing for explaining the principle of detecting a concentration of oxygen by the upstream air-fuel ratio sensor shown in FIG. 1.

As shown in FIG. 5, the upstream air-fuel ratio sensor 64 outputs an output value according to "a concentration of oxygen of the upstream-side gas to be detected" with (by) utilizing the above mentioned oxygen cell characteristic, when the air-fuel ratio of the upstream-side gas to be detected is a rich-side air-fuel ratio richer than the stoichiometric air-fuel ratio. Specifically, when the air-fuel ratio of the upstream-side gas to be detected is the rich-side air-fuel ratio richer than the stoichiometric air-fuel ratio, a large amount of unburnt products (HC, CO, and H2, etc.) contained in the upstream gas to be detected reach the exhaust gas side electrode layer 64b through the diffusion resistance layer 64d. At this time, since a difference in oxygen concentration between the exhaust gas side electrode layer 64b and the atmospheric air side electrode layer 64c becomes large, the solid electrolyte layer 64a functions as the oxygen cell. The applied voltage V (=Vp) is set to be smaller than an electromotive force of the oxygen cell.

Accordingly, oxygen molecules existing in the air chamber 64g receive electrons at the atmospheric air side electrode layer 64c so as to become oxygen ions. The oxygen ions pass through the solid electrolyte layer 64a and move to the exhaust gas side electrode layer 64b. Then, the oxygen ions oxidize the unburnt products at the exhaust gas side electrode layer 64b with releasing the electrons. As a result, an electrical current I flows from the negative electrode of the electric power supply 64h to the positive electrode of the electric power supply 64h through the exhaust gas side electrode layer 64b, the solid electrolyte layer 64a, and the atmospheric air side electrode layer 64c.

The magnitude of the electrical current I is determined based on an amount of the oxygen ions which reach the exhaust gas side electrode layer 64b from the atmospheric air side electrode layer 64c through the solid electrolyte layer 64a. As described above, the oxygen ions are used to oxidize the unburnt products at the exhaust gas side electrode layer 64b. Accordingly, as the amount of the unburnt products which reach the exhaust gas side electrode layer 64b through the diffusion resistance layer 64d by diffusion becomes greater, the amount of the oxygen ions passing through the solid electrolyte layer 64a becomes greater. In other words, as the air-fuel ratio is smaller (as an amount of the unburnt products is greater due to the richer air-fuel ratio), the magnitude of the electric current I is larger. However, because of the existence of the diffusion resistance layer 64d, the amount of the unburnt products which reach the exhaust gas side electrode layer 64b is limited. Thus, the electrical current I becomes an constant value Ip according to the air-fuel ratio. The upstream air-fuel ratio sensor 64 outputs the output value AFU which is proportional to the limiting current Ip. It should be noted that, since the engine 10 is a diesel engine, an air-fuel ratio of the mixture supplied to the engine is considerably larger than stoichiometric air-fuel ratio (i.e., lean air-fuel ratio). Accordingly, the upstream air-fuel ratio sensor 64 scarcely utilizes the oxygen cell characteristic.

Referring back to FIG. 1, the exhaust gas temperature sensor 65 is disposed at "the position downstream of the SCR catalyst 44" and "the position upstream of the muffler 45" of the exhaust pipe 42 (exhaust passage). Accordingly, the exhaust gas temperature sensor 65 is configured so as to output a signal Tex representing a temperature of an exhaust gas flowing out from the SCR catalyst 44.

The downstream air-fuel ratio sensor 66 is disposed at "the position downstream of the SCR catalyst 44" and "the position upstream of the muffler 45" of the exhaust pipe 42 (exhaust passage). The downstream air-fuel ratio sensor 66 has a structure similar to a structure of the upstream air-fuel ratio sensor 64. That is, the downstream air-fuel ratio sensor 66 is "a wide range air-fuel ratio sensor of a limiting current type having a diffusion resistance layer".

More specifically, as shown by numerals in parentheses in FIG. 2, the downstream air-fuel ratio sensor 66 includes a solid electrolyte layer 66a, an exhaust gas side electrode layer 66b, an atmospheric air side electrode layer 66c exposed in a space (an air chamber 66g) to which atmosphere is introduced, a diffusion resistance layer 66d, and a heater 66f. The air chamber 66g is defined by a dense septum wall section 66e. The exhaust gas side electrode layer 66b and the atmospheric air side electrode layer 66c are formed on both surfaces of the solid electrolyte layer 66a in such a manner that they oppose to each other so as to sandwich the solid electrolyte layer 66a. The exhaust gas side electrode layer 66b is covered by the diffusion resistance layer 66d.

The downstream air-fuel ratio sensor 66, similarly to the upstream air-fuel ratio sensor 64, outputs an output value AFD which varies in accordance with "a concentration (or a partial pressure) of oxygen at the exhaust gas side electrode layer 66b" of "a gas which has reached the exhaust gas side electrode layer 66b after reaching an outer surface of the diffusion resistance layer 66d and passing through the diffusion resistance layer 66d". It should be noted that it is designed that "the output value AFD of the downstream air-fuel ratio sensor 66" for "an exhaust gas, whose oxygen concentration is predetermined, and which contains no ammonia" is equal to "the output value AFU of the upstream air-fuel ratio sensor 64" for "the same exhaust gas".

Referring back to FIG. 1, the accelerator opening sensor 67 detects an operation amount of an accelerator pedal AP so as to output a signal Accp representing the operation amount of the accelerator pedal AP.

The electric controller 70 is a well-known microcomputer, which includes "a CPU, a ROM, a RAM, a Back-up RAM which stores data while power is supplied and which retains the stored data even while power is not supplied, an interface including an AD converter, and so on".

The interface of the electric controller 70 is connected to the sensors 61 to 67 and supplies signals from the sensors 61 to 67 to the CPU. The interface sends out instruction signals (drive signals) to each of the injectors 21 and the urea-water injector 55, etc.

The CPU of the electric controller 70 determines a fuel injection amount based on the signal Accp representing the operation amount of the accelerator pedal and the engine rotational speed NE. The CPU sends an instruction signal to the injector 21 so that the fuel of the determined fuel injection amount is injected into each of the combustion chambers. By the fuel injection, the air-fuel ratio of the mixture supplied to the engine 10 is controlled so as to be a lean side air-fuel ratio compared with stoichiometric air-fuel ratio (an air fuel ratio larger than the stoichiometric air-fuel ratio).

(Detection Principle of an Ammonia-Amount-Relating-Value)

Next will be described a detection principle of "an ammonia-amount-relating-value", which the first exhaust purifying apparatus adopts. The first exhaust purifying apparatus obtains a value $DNH_3$ representing "a concentration of ammonia" as the ammonia-amount-relating-value.

The urea ($CO(NH_2)_2$ contained in the urea-water which is injected and supplied into the exhaust pipe 42 (exhaust passage) from the urea-water injector 55 changes into ammonia ($NH_3$) and carbon dioxide ($CO_2$) in the exhaust pipe 42 by hydrolysis according to the following formula.

$$H_2N\text{---}CO\text{---}NH_2 + H_2O \rightarrow CO_2 + 2NH_3 \quad (4)$$

Figure 6:
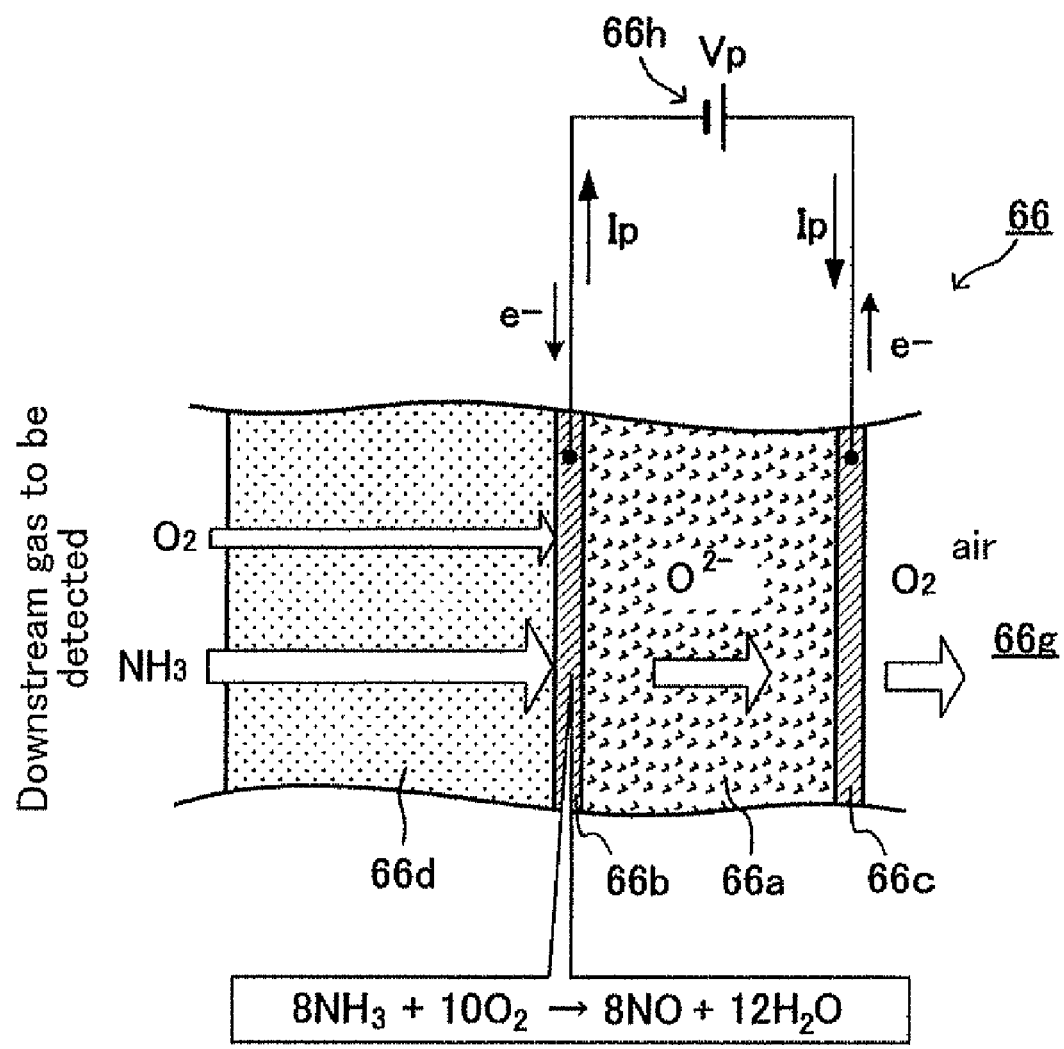
FIG. 6 is a drawing for explaining a principle of obtaining an ammonia-amount-relating-value by a downstream air-fuel ratio sensor shown in FIG. 1.

The ammonia thus produced flows into the SCR catalyst 44 together with the exhaust gas. The ammonia reduces (or purifies) nitrogen oxides contained in the exhaust gas in the SCR catalyst 44, as shown by the formulas of (1)-(3) described above. At this time, if an amount of urea-water is excessive for the nitrogen oxides flowed into the SCR catalyst 44, the ammonia produced from the urea-water can not be completely consumed in the SCR catalyst 44. That is, the ammonia which is not used for reducing the nitrogen oxides flows out from the SCR catalyst 44 to downstream of the SCR catalyst 44, and reach the outer surface of the diffusion resistance layer 66d of the downstream air-fuel ratio sensor 66. In this case, the gas which reaches the outer surface of the diffusion resistance layer 66d (a downstream gas to be detected) contains oxygen (oxygen molecules) and the ammonia (ammonia molecules). "The oxygen molecules and the ammonia molecules" contained in the downstream gas to be detected diffuse in the diffusion resistance layer 66d to reach the exhaust gas side electrode layer 66b, as shown in FIG. 6.

Meanwhile, an ammonia molecule ($NH_3$) is smaller in its molecular weight and its molecular diameter than an oxygen molecule ($O_2$). Therefore, diffusion speed of an ammonia molecule in the diffusion resistance layer 66d is higher than diffusion speed of an oxygen molecule in the diffusion resistance layer 66d. In other words, "a sum of moving distance (referred to as "mean diffusion distance") required for the oxygen molecule to reach the exhaust gas side electrode layer 66b while passing through the diffusion resistance layer 66d with colliding with grains constituting the diffusion resistance layer 66d" is greater than "a sum of moving distance (mean diffusion distance) required for the ammonia molecule to reach the exhaust gas side electrode layer 66b while passing through the diffusion resistance layer 66d".

Accordingly, if the downstream gas to be detected contains ammonia molecules, the ammonia molecules pass through the diffusion resistance layer 66d and reach the exhaust gas side electrode layer 66b more preferentially than the oxygen molecules contained in the downstream gas to be detected. Thereafter, the ammonia molecules combine with oxygen at the exhaust gas side electrode layer 66b, as shown by the formula (5) described below. That is, the ammonia is oxidized and oxygen is consumed at the exhaust gas side electrode layer 66b.

$$8NH_3 + 10O_2 \rightarrow 8NO + 12H_2O \qquad (5)$$

As a result, the output value AFD (=AFD1) of the downstream air-fuel ratio sensor 66 when a concentration of oxygen of the downstream gas to be detected is a given concentration and the downstream gas to be detected contains ammonia becomes a value showing that the downstream gas to be detected is a gas whose concentration of oxygen is smaller (richer gas)", compared with the output value AFD (=AFD2) of the downstream air-fuel ratio sensor 66 when a concentration of oxygen of the downstream gas to be detected is the given concentration and the downstream gas to be detected contains no ammonia. That is, because the output value AFD becomes greater as the concentration of oxygen becomes greater, AFD1 becomes smaller than AFD2.

Figure 7:
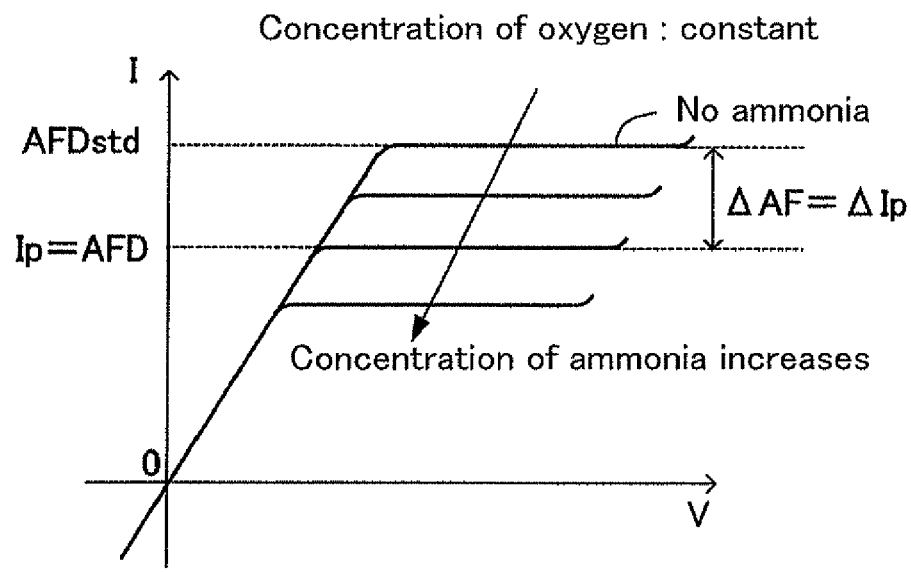
FIG. 7 is a graph showing "a relationship between a voltage supplied to the downstream air-fuel ratio sensor and a limiting current value (an output value of the downstream air-fuel ratio sensor)" for various concentrations of ammonia.

Accordingly, as shown in FIG. 7, even when the concentration of the oxygen on the downstream gas to be detected is constant, the output value AFD (the limiting current Ip) of the downstream air-fuel ratio sensor 66 decreases as the concentration of ammonia of the downstream gas to be detected increases. In other words, the output value AFD becomes a value which shows that "the concentration of oxygen of the downstream gas to be detected is smaller (the gas is richer)", as the concentration of ammonia of the downstream gas to be detected increases.

In view of the above, the first exhaust purifying apparatus stops injecting or supplying the urea-water, when a first predetermined condition is satisfied. This allows the gas containing no ammonia to reach the downstream air-fuel ratio sensor 66. That is, the concentration of ammonia of the downstream gas to be detected becomes zero. The apparatus stores the output value AFD of the downstream air-fuel ratio sensor 66 under this state as a reference value AFDstd. The reference value AFDstd is also referred to as "a first output value" for convenience. In this manner, the value (AFDstd) which varies in accordance with the concentration of oxygen of "the exhaust gas in a state where the nitrogen oxides contained in the gas has not been purified by the SCR catalyst 44" is obtained as the first output value.

Subsequently, the first exhaust purifying apparatus injects a certain (or a predetermined) amount of urea-water from the urea-water injector 55, and it obtains the output value AFD of the downstream air-fuel ratio sensor 66. At this point of time, if the urea-water is not excessive (the urea-water is insufficient), no ammonia flows out from the SCR catalyst 44 to downstream of the SCR catalyst 44. Thus, the obtained value AFD is equal to the reference value AFDstd. To the contrary, if the urea-water is excessive and therefore the ammonia flows out of the SCR catalyst 44 to downstream of the SCR catalyst 44 (the ammonia slip occurs), the obtained output value AFD becomes smaller than the reference value AFDstd. In addition, the difference $\Delta AF$ (=AFDstd−AFD) between "the reference value AFDstd" and "the output value AFD" becomes greater, as the concentration of the ammonia becomes greater.

Figure 8:
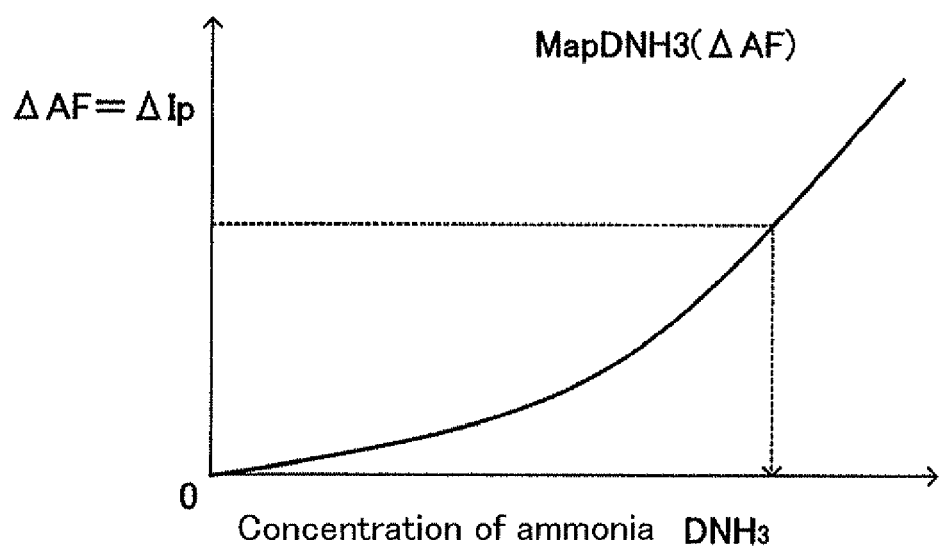
FIG. 8 is a graph showing a relationship between a variation (decreasing) amount in the output of the downstream air-fuel ratio sensor and a concentration of ammonia.

Accordingly, the first exhaust purifying apparatus obtains the difference $\Delta AF$ (=AFDstd−AFD) between "the reference value AFDstd" and "the obtained output value AFD" and applies the difference $\Delta AF$ to a table MapDNH3($\Delta AF$) to obtain "the concentration of ammonia $DNH_3$". The table MapDNH3($\Delta AF$), as shown in FIG. 8, defines a relationship between the difference $\Delta AF$ and the concentration of ammonia $DNH_3$. The table MapDNH3($\Delta AF$) is prepared based on data obtained by experiments beforehand and is stored in the ROM of the electric controller 70. In this manner, the first exhaust purifying apparatus obtains "the ammonia-amount-relating-value (here, the concentration of ammonia $DNH_3$)" which is a value relating to the amount of ammonia flowing out of the SCR catalyst 44.

(Actual Operation)

Next will be described an actual operation of the first exhaust purifying apparatus. The CPU of the electric controller 70 is configured in such a manner that it repeatedly executes "a reference value (first value) obtaining routine" shown in FIG. 9 every elapse of a predetermined time. Accordingly, at a predetermined timing, the CPU starts processing from step 900 of FIG. 9 and determines whether or not the first predetermined condition (the first output value obtaining condition) is satisfied at step 910.

The first predetermined condition is a condition which is satisfied when it is considered to be necessary to renew (or update) the reference value AFDstd described above. The first predetermined condition may be determined to be a condition which is satisfied, when one of conditions of (1)-(4) described below is satisfied or when at least one condition of two or more arbitrary conditions of these is satisfied. It should be noted that the first predetermined condition in the present example is (1) below. However, the first predetermined condition is not limited to it and may be different conditions.

—The First Predetermined Condition—

(1) A predetermined constant time has elapsed from the timing when the previous reference value AFDstd was obtained.

(2) The load of the engine 10 (e.g., the operation amount Accp of the accelerator pedal, a fuel injection amount, or an amount of intake air Ga per one combustion cycle) has changed from the load when "the previous reference value AFDstd was obtained" by an amount greater than a predetermined threshold load.

(3) The engine rotational speed NE has changed from the engine rotational speed NE when "the previous reference value AFDstd was obtained" by an amount greater than a predetermined threshold speed.

(4) The concentration DNOx of the nitrogen oxides detected by the NOx sensor 63 has changed from the concentration DNOx of the nitrogen oxides when "the previous reference value AFDstd was obtained" by an amount greater than a predetermined threshold concentration.

When the first predetermined condition is not satisfied, the CPU makes a determination of "No" at step 910, then directly proceeds to step 995 to end the present routine tentatively. To the contrary, when the first predetermined condition is satisfied, the CPU makes a determination of "Yes" to proceed to step 920 at which the CPU stops injecting or supplying the urea-water. That is, an injection amount URInj of the urea-water is set to "0" to stop sending the injection instruction signal to urea-water injector 55.

Subsequently, the CPU proceeds to step 930 at which the CPU monitors whether or not a first predetermine time period has elapsed since the urea-water injection is stopped by the processing of step 920. The first predetermine time period is set to a period a little longer than a duration from the timing when the urea-water injection is stopped to the timing when the ammonia disappears in the SCR catalyst 44.

When the first predetermined time period has elapsed since the urea-water injection is stopped, the CPU makes a determination of "Yes" at step 930 to proceed to step 940 at which the CPU obtains (and stores) the output value AFD of the downstream air-fuel ratio sensor 66, as the reference value AFDstd. The reference value AFDstd is referred to as "the first output value AF1" for convenience. Subsequently, the CPU proceeds to step 995 to end the present routine tentatively.

Figure 9:
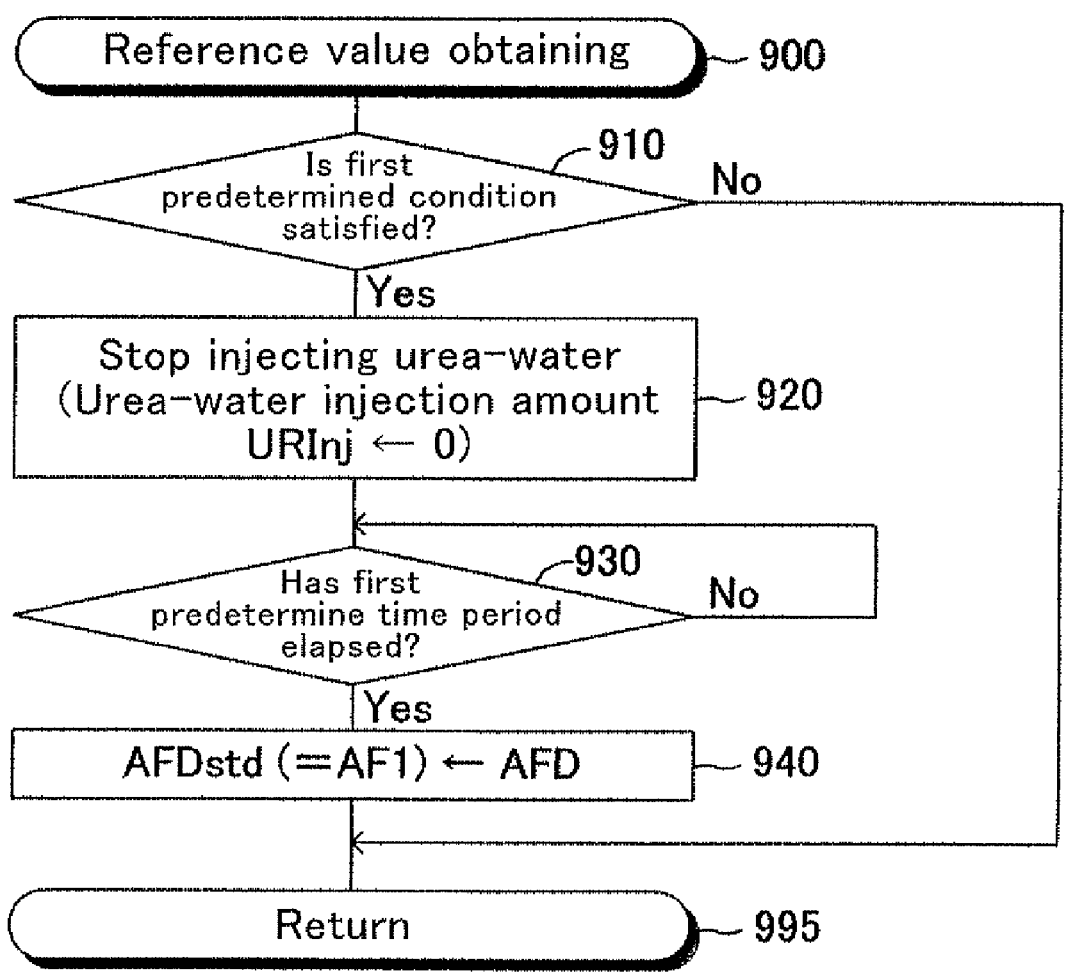
FIG. 9 is a flowchart showing a program executed by a CPU of the first exhaust purifying apparatus.
Figure 10:
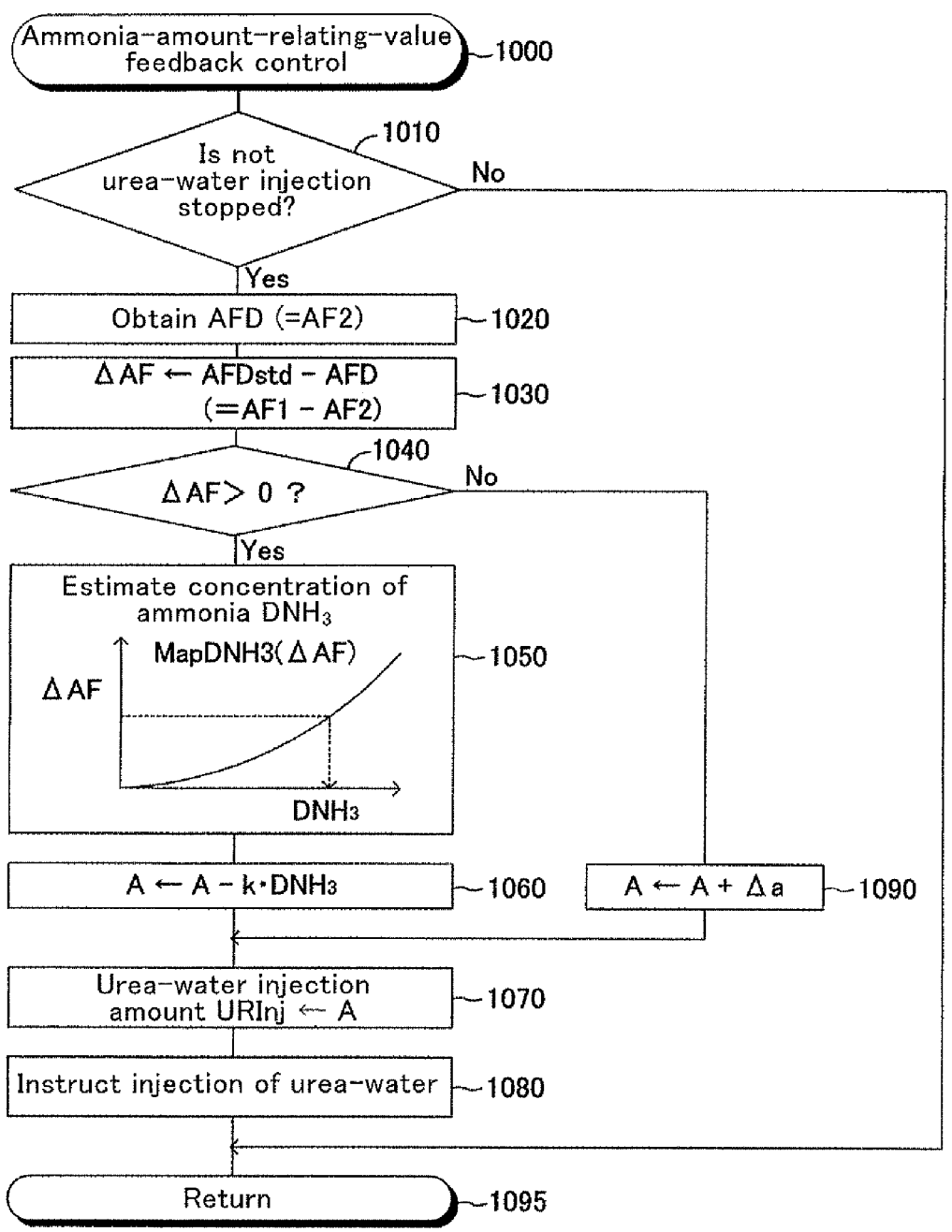
FIG. 10 is a flowchart showing a program executed by the CPU of the first exhaust purifying apparatus.

Further, the CPU is configured in such a manner that it repeatedly executes "a feedback control routine of ammonia-amount-relating-value routine" shown in FIG. 10 every elapse of a predetermined time. Accordingly, at a predetermined timing, the CPU starts processing from step 1000 of FIG. 10 to proceed to step 1010 at which the CPU determines whether or not "the urea-water injection is not stopped by the processings of the routine of FIG. 9" at the present time.

At this point of time, if the urea-water injection is stopped, the CPU makes a determination of "No" at step 1010 to directly proceed to step 1095 so as to end the present routine tentatively. To the contrary, if the urea-water injection is not stopped at the present time, the CPU makes a determination of "Yes" at step 1010 to proceed to step 1020 to obtain the output value AFD of the downstream air-fuel ratio sensor 66. The output value AFD obtained at step 1020 is referred to as "the second output value AF2" for convenience.

Subsequently, the CPU proceeds to step 1030 at which the CPU obtains the difference $\Delta AF$ (=AFDstd−AFD=AF1−AF2) by subtracting "the output value AFD (the second output value AF2) obtained at step 1020" from "the reference value AFDstd (the first output value AF1) obtained at step 940 in FIG. 9". The difference $\Delta AF$ is also referred to as a downstream air-fuel ratio sensor output value decreasing amount.

Subsequently, the CPU proceeds to step 1040 at which the CPU determines whether or not the difference $\Delta AF$ is greater than "0". In other words, the CPU determines whether or not the output value AFD is smaller than the reference value AFDstd. When the difference $\Delta AF$ is a positive value (i.e. when the output value AFD is smaller than the reference value), it is presumed that ammonia is flowing out from the SCR catalyst 44, as described above. Accordingly, when the output value AFD is smaller than the reference value, the CPU makes a determination of "Yes" at step 1040 to proceed to step 1050 at which the CPU obtains "the concentration of ammonia $DNH_3$" by applying the difference $\Delta AF$ to the table MapDNH3($\Delta AF$) shown in a block of step 1050 and in FIG. 8".

Subsequently, the CPU proceeds to step 1060 at which the CPU updates (renews) the urea-water supply amount A to be supplied at the present time (a supply amount of the additive agent). Specifically, the CPU stores, as an updated urea-water supply amount A, a value obtained by subtracting "a product of the concentration of ammonia $DNH_3$ and a coefficient k" from "the urea-water supply amount A at the present". It should be noted that the coefficient k may be constant or a value which becomes larger as the intake air amount Ga or the operation amount Accp of the accelerator pedal becomes larger.

Subsequently, the CPU proceeds to step 1070 at which the CPU sets the urea-water injection amount URInj at (to be equal to) the urea-water supply amount A. Thereafter, the CPU proceeds to step 1080 to send the instruction signal to the urea-water injector 55 so that the urea-water of the urea-water injection amount URInj is injected from the urea-water injector 55. Then, the CPU proceeds to step 1095 to end the present routine tentatively.

Meanwhile, if the difference $\Delta AF$ is less than or equal to "0" when the CPU processes step 1040 (i.e., when the output value AFD is equal to or more than the reference value AFDstd), it is presumed that the ammonia does not flow out from the SCR catalyst 44. In other words, it is presumed that the amount of urea-water is insufficient and thus the amount of ammonia supplied to the SCR catalyst 44 is insufficient.

For the reason above, the CPU, in this case, makes a determination of "No" at step 1040 to proceed to step 1090 at which the CPU stores, as "the updated urea-water supply amount A", a value obtained by adding "a constant small positive value $\Delta a$" to "the urea-water supply amount A at the present". Subsequently, the CPU performs processings of step 1070 to step 1080. As a result, when the ammonia slip is not occurring, the urea-water supply amount is gradually increased every time the routine shown in FIG. 10 is executed. It should be noted that the value $\Delta a$ may be constant or a value which becomes larger as the intake air amount Ga or the operation amount Accp of the accelerator pedal becomes larger.

As described above, the first exhaust purifying apparatus comprises a first output value obtaining means for obtaining a value which varies in accordance with the concentration of "oxygen" of "the exhaust gas which is in a state where nitrogen oxides contained in the exhaust gas have not been purified by said SCR catalyst 44", i.e., "the first output value AF1 (the reference value AFDstd)" (See step 940 in FIG. 9).

In other words, the first output value obtaining means is configured so as to obtain "the first output value AF1 (the reference value AFDstd)" which is "the output value AFD of the downstream air-fuel ratio sensor 66" when (while) the additive agent supplying means (the urea-water supplying device 50, the urea-water injector 55) does not supply (is not supplying) the additive agent (the urea-water).

In addition, the first exhaust purifying apparatus comprises a second output value obtaining means which obtains "the second output value AF2" which is "the value based on the output value AFD of the downstream air-fuel ratio sensor 66" when (while) the additive agent supplying means supplies (is supplying) the additive agent (See step 1020 in FIG. 10).

In other words, the second output value obtaining means is configured so as to obtain the second output value AF2 which is "the output value AFD of the downstream air-fuel ratio sensor 66" when (while) the additive agent supplying means supplies (is supplying) the additive agent.

Furthermore, the first exhaust purifying apparatus comprises,

"ammonia-amount-relating-value obtaining means" which obtains the ammonia-amount-relating-value (the concentration of ammonia) which relates to the amount of ammonia which flows out from said SCR catalyst 44, based on "the difference $\Delta AF$ between the first output value AF1 and the second output value AF2" (See the determining result in step 1040 in FIG. 10 and step 1050); and additive agent amount control means, which determines the amount A of the additive agent (the urea-water) to be supplied, based on the obtained ammonia-amount-relating-value, and which sends to the additive agent supplying means the instruction to supply the determined amount A of the additive agent (the urea-water) (See steps 1060-1090).

In addition, the additive agent amount control means is configured so as to send to the additive agent supplying means the instruction to stop supplying the additive agent (the urea-water) (See step 920 in FIG. 9), in order to make the first output value obtaining means obtain the first output value AF1 (i.e., to make it execute step 940 in FIG. 9), when the first predetermined condition is satisfied (See step 910 in FIG. 9).

As described above, the difference $\Delta AF$ between the first output value and the second output value varies depending on the amount of the ammonia which flows out from the SCR catalyst 44 (i.e., the concentration of ammonia). Accordingly, the first exhaust purifying apparatus can obtain the ammonia-amount-relating-value by using the inexpensive downstream air-fuel ratio sensor 66, instead of disposing an additional expensive NOx sensor (which is the same sensor as the sensor 63) at a position downstream of the SCR catalyst 44. As a result, the inexpensive exhaust purifying apparatus can be provided.

It should be noted that the first exhaust purifying apparatus comprises the air flowmeter 61, the NOx sensor 63, the upstream air-fuel ratio sensor 64, and the exhaust gas temperature sensor 65, however, at least one of these sensors can be omitted.

Second Embodiment

Next, an exhaust purifying apparatus for the internal combustion engine (hereinafter, simply referred to as "a second exhaust purifying apparatus") according to a second embodiment of the present invention will be described. The second exhaust purifying apparatus differs from the first exhaust purifying apparatus in that the CPU of the electric controller 70 executes "a routine shown as a flowchart in FIG. 11" in place of "FIGS. 9 and 10". Accordingly, the following description specially focuses on this point of difference. It should be noted that each step in FIG. 11 at which the same processing is performed as each step shown in FIG. 10 is given the same numeral as one given to such step shown in FIG. 10. Detail descriptions for these steps may be omitted appropriately.

Figure 11:
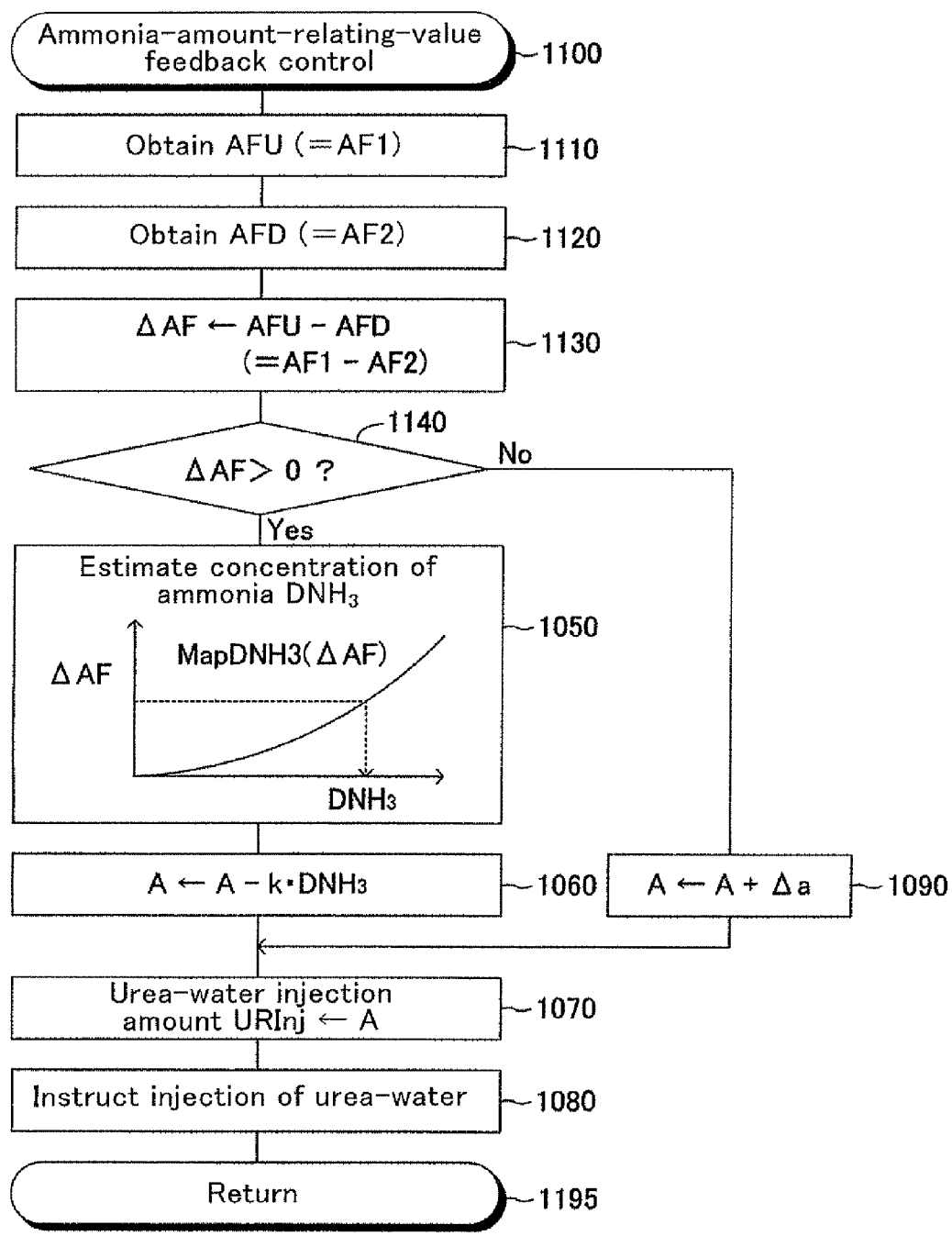
FIG. 11 is a flowchart showing a program executed by a CPU of an exhaust purifying apparatus according to a second embodiment of the present invention (a second exhaust purifying apparatus)

The CPU is configured so as to repeatedly execute a routine shown in FIG. 11 every elapse of a predetermined time. Accordingly, at a predetermined timing, the CPU starts processing from step 1100 of FIG. 11, and performs processings from step 1110 to step 1130 described below.

Step 1110: The CPU obtains the output value AFU of the upstream air-fuel ratio sensor 64. The exhaust gas which has reached the upstream air-fuel ratio sensor 64 is "the exhaust gas in the state where the nitrogen oxides contained in the exhaust gas has not been purified by the SCR catalyst 44". The output value AFU is therefore a value which varies depending on the concentration of oxygen of such exhaust gas. That is, the output value AFU obtained at step 1110 is a value corresponding to the aforementioned reference value AFDstd and the aforementioned first output value AF1.

Step 1120: The CPU obtains the output value AFD of the downstream air-fuel ratio sensor 66. As described later, the urea-water is always supplied in the second exhaust purifying apparatus. Accordingly, the exhaust gas, which has passed through the SCR catalyst 44 while the urea-water is being supplied to the SCR catalyst 44, reaches the downstream air-fuel ratio sensor 66. The output value AFD obtained at step 1120 is therefore the aforementioned second output value.

Step 1130: The CPU calculates a difference $\Delta AF$ (=AFU−AFD) between "the obtained output value AFU" and "the obtained output value AFD".

As described above, it is designed that "the output value AFD of the downstream air-fuel ratio sensor 66" for "an exhaust gas, whose oxygen concentration is predetermined, and which contains no ammonia" is equal to "the output value AFU of the upstream air-fuel ratio sensor 64" for "the same gas". Accordingly, when the ammonia is not flowing out from the SCR catalyst 44, the output value AFD coincides with the output value AFU. To the contrary, the output value AFD decreases depending on the concentration of the ammonia, when the ammonia is flowing out from the SCR catalyst 44. In this case, the difference $\Delta AF$ (=AFU−AFD) is therefore positive and becomes greater as the concentration of the ammonia becomes greater.

In view of the above, the CPU determines whether or not the difference $\Delta AF$ is equal to or more than "0" at step 1140 following step 1130. When the difference $\Delta AF$ is equal to or more than "0", the CPU makes a determination of "Yes" at step 1140 to proceed to step 1050 at which the CPU applies the difference $\Delta AF$ to "the table MapDNH3($\Delta AF$)" so as to obtain "the concentration of ammonia $DNH_3$".

Subsequently, the CPU proceeds to step 1060 at which the CPU stores, "as the updated urea-water supply amount A", a value obtained by subtracting "a product of the concentration of ammonia $DNH_3$ and the coefficient k (k·$DNH_3$)" from "the urea-water supply amount A at the present".

Subsequently, the CPU proceeds to step 1070 at which the CPU sets the urea-water injection amount URInj at the urea-water supply amount A. Thereafter, the CPU proceeds to step 1080 to send the instruction signal to the urea-water injector 55 so that the urea-water of the urea-water injection amount URInj is injected from the urea-water injector 55. Then, the CPU proceeds to step 1195 to end the present routine tentatively.

Meanwhile, the difference $\Delta AF$ is less than or equal to "0" when the CPU processes step 1140 (i.e., when the output value AFD is equal to or more than the output value AFU), it is presumed that the ammonia does not flow out from the SCR catalyst 44. In other words, it is presumed that the amount of urea-water is insufficient and thus the amount of ammonia supplied to the SCR catalyst 44 is insufficient.

For the reason above, the CPU, in this case, makes a determination of "No" at step 1140 to proceed to step 1090 at which the CPU stores, as "the updated urea-water supply amount A", the value obtained by adding "a constant small positive value $\Delta$" to "the urea-water supply amount A at the present". Subsequently, the CPU performs processings of step 1070 and step 1080. As a result, when the ammonia slip is not occurring, the urea-water supply amount is gradually increased every time the routine shown in FIG. 11 is executed.

As described above, the second exhaust purifying apparatus comprises:

first output value obtaining means for obtaining the value which varies in accordance with the concentration of "oxygen" of "the exhaust gas which is in a state where nitrogen oxides contained in the exhaust gas have not been purified by said SCR catalyst 44" (a value based on the output value AFU of the upstream air-fuel ratio sensor, which is the output value AFU itself in the present embodiment), i.e., for obtaining the first output value AF1 (See step 1110 in FIG. 11);

second output value obtaining means for obtaining "the second output value AF2" which is a value based on the output value of the downstream air-fuel ratio sensor AFD when (while) the additive agent is supplied (or is being supplied) (See step 1120);

ammonia-amount-relating-value obtaining means for obtaining the ammonia-amount-relating-value (the concentration of ammonia) based on the difference $\Delta AF$ between the first output value AF1 and the second output value AF2 (See the determining result in step 1140 and step 1050 in FIG. 11); and additive agent amount control means for determining the amount A of the additive agent (the urea-water) to be supplied based on the obtained ammonia-amount-relating-value (the concentration of ammonia) (See "step 1060 and step 1090" in FIG. 11), and for sending to the additive agent supplying means the instruction to supply "the determined amount A of the additive agent (the urea-water)" (See "step 1070 and step 1080" in FIG. 11).

The exhaust gas in "a state where the nitrogen oxides contained in the exhaust gas has not been purified by the SCR catalyst 44" arrives always at the outer surface of the diffusion resistance layer 64d of the upstream air-fuel ratio sensor 64. Thus, it is not necessary to stop supplying the urea water (the additive agent) in order to obtain the first output value, if "a value based on the output value of the upstream air-fuel ratio sensor AFU" is obtained as "the first value" which corresponds to the above described the reference value AFDstd that the first exhaust purifying apparatus uses. Accordingly, the second exhaust purifying apparatus can always supply "the ammonia which is produced from the urea water" to "the SCR catalyst 44", and it can therefore control the amount of the urea-water appropriately while purifying the nitrogen oxides.

Third Embodiment

Next, an exhaust purifying apparatus for the internal combustion engine (hereinafter, simply referred to as "a third exhaust purifying apparatus") according to a third embodiment of the present invention will be described. The third exhaust purifying apparatus obtains the ammonia-amount-relating-value, using the output value AFU of the upstream air-fuel ratio sensor 64 and the output value AFD of the downstream air-fuel ratio sensor 66, similarly to the second exhaust purifying apparatus. In addition, the third exhaust purifying apparatus compensates for a difference in output characteristic between the upstream air-fuel ratio sensor 64 and the downstream air-fuel ratio sensor 66.

Figure 12:
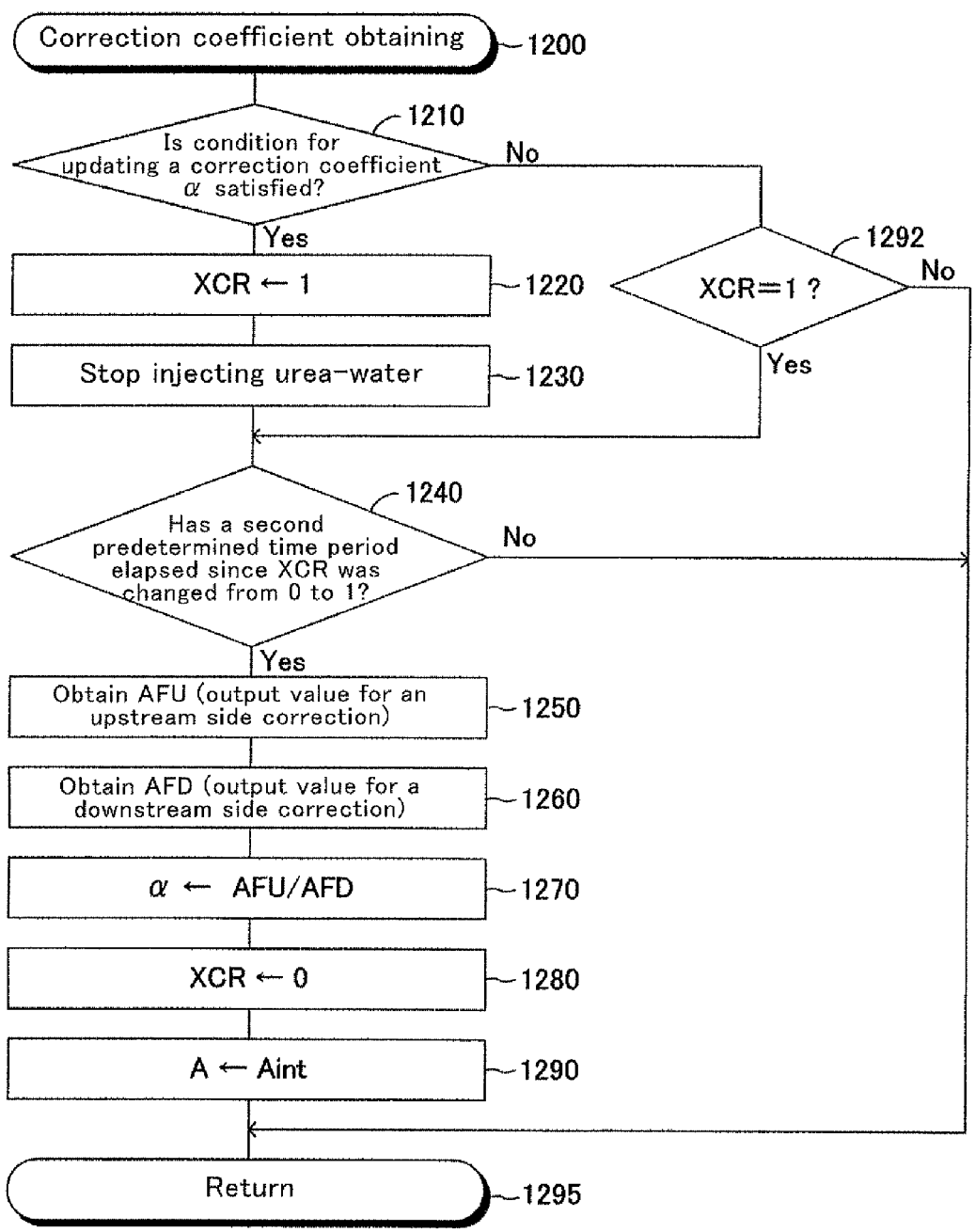
FIG. 12 is a flowchart showing a program executed by a CPU of an exhaust purifying apparatus according to a third embodiment of the present invention (a third exhaust purifying apparatus)
Figure 13:
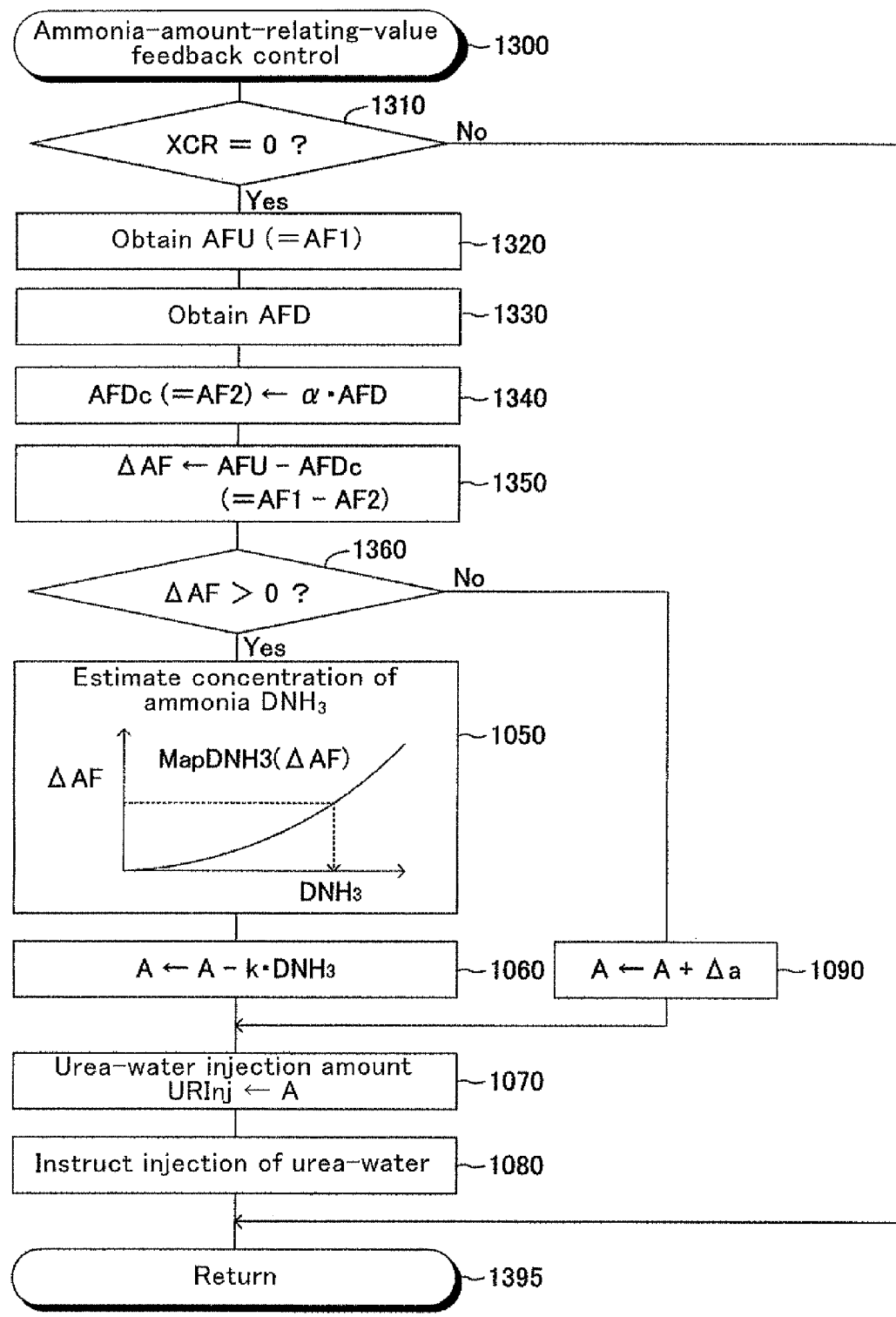
FIG. 13 is a flowchart showing a program executed by the CPU of the third exhaust purifying apparatus.

The third exhaust purifying apparatus differs from the first exhaust purifying apparatus in that the CPU of the electric controller 70 executes "routines shown as flowcharts in "FIGS. 12 and 13" in place of "FIGS. 9 and 10". Accordingly, the following description specially focuses on this point of difference. It should be noted that each step in FIG. 13 at which the same processing is performed as each step shown in FIG. 10 is given the same numeral as one given to such step shown in FIG. 10. Detail descriptions for these steps may be omitted appropriately.

The CPU is configured so as to repeatedly execute "a correction coefficient obtaining routine" shown in FIG. 12 every elapse of a predetermined time. Accordingly, at a predetermined timing, the CPU starts processing from step 1200 of FIG. 12, and determines whether or not a condition (a correction coefficient updating condition) for updating (renewing) a correction coefficient α is satisfied at step 1210. The correction coefficient updating condition is referred to as "a second predetermined condition" for convenience. The correction coefficient updating condition in the present example is that a predetermined constant time period has elapsed since a timing at which the correction coefficient α was previously updated. It should be noted that the correction coefficient updating condition is not limited to the above, but may be the same as the aforementioned first predetermined condition or another conditions (e.g., a condition which is satisfied by determining whether or not the both the upstream air-fuel ratio sensor 64 and the downstream air-fuel ratio sensor 66 are activated for the first time after a start of the engine).

Here, it is assumed that the correction coefficient updating condition is satisfied. In this case, the CPU makes a determination of "Yes" at step 1210 to proceed to step 1220 at which the CPU sets a value of correction coefficient updating flag XCR at "1". The correction coefficient updating flag XCR shows that a control (stopping the urea-water injection) for updating the correction coefficient α is being performed when the value of the flag XCR is "1", and the control for updating the correction coefficient α is not being performed when the value of the flag XCR is "0". It should be noted that the value of correction coefficient updating flag XCR is set at either "1" or "0", when an ignition key switch (not shown) is turned on from off.

Subsequently, the CPU proceeds to step 1230 at which the CPU stops injecting (supplying) the urea-water. That is, the injection amount URInj of the urea-water is set to "0" to stop sending the injection instruction signal to urea-water injector 55.

Subsequently, the CPU proceeds to step 1240 at which the CPU determines whether or not a second predetermined time period has elapsed since a timing (hereinafter, the timing is referred to as "the flag changing timing") at which the value of the flag XCR was changed from "0" to "1". The second predetermined time period is set to a period a little longer than a duration from the timing when the urea-water injection is stopped to the timing when the ammonia disappears in the SCR catalyst 44.

The present timing is immediately after the value of the flag XCR is set at "1" at step 1220. Thus, the CPU makes a "No" determination at step 1240 to directly proceed to step 1295 so as to end the present routine tentatively.

Meanwhile, the CPU is configured so as to repeatedly execute "a feedback control routine of the ammonia-amount-relating-value" shown in FIG. 13 every elapse of a predetermined time. Accordingly, at a predetermined timing, the CPU starts processing from step 1300 of FIG. 13 to proceed step 1310 at which the CPU determines whether or not the value of the flag XCR is "0". At the present time, the value of the flag XCR is "1". The CPU therefore makes a determination of "No" at step 1310 to directly proceed to step 1395 so as to end the present routine tentatively.

Thereafter, the CPU repeatedly executes the routine shown in FIG. 12 every elapse of the predetermined time. Here, it is assumed that the correction coefficient updating condition is continuously satisfied. In this case, the CPU performs processings from step 1200 to step 1230 and proceeds to step 1240 at which the CPU makes a determination of "No" so as to end the present routine tentatively, until the second predetermined time period has elapsed since the flag changing timing.

When the CPU starts processing from step 1200 of FIG. 12 immediately after the timing at which the second predetermine time period has elapsed since the flag changing timing, the CPU makes a determination of "Yes" at step 1240 which follows "step 1210 to step 1230" so as to perform processings from step 1250 to step 1290 described below.

Step 1250: The CPU obtains the output value AFU of the upstream air-fuel ratio sensor 64. The exhaust gas which has reached the upstream air-fuel ratio sensor 64 is "the exhaust gas in the state where the nitrogen oxides contained in the exhaust gas has not been purified by the SCR catalyst 44". Accordingly, the output value AFU is a value which varies depending on the concentration of oxygen of such exhaust gas. Further, the output value AFU obtained at step 1250 is the output of the upstream air-fuel ratio sensor 64 when "the additive agent (the urea-water) is not supplied". The output value AFU obtained at step 1250 is referred to as "an output value for an upstream side correction", for convenience.

Step 1260: The CPU obtains the output value AFD of the downstream air-fuel ratio sensor 66. In this case, the urea-water is not being supplied. Thus, the downstream gas to be detected is also "the exhaust gas in the state where the nitrogen oxides contained in the exhaust gas has not been purified by the SCR catalyst 44". In other words, the downstream gas to be detected is a gas whose concentration of oxygen is the same as the concentration of oxygen which the upstream air-fuel ratio sensor 64 is detecting and which contains no ammonia. The output value AFD obtained at step 1260 is the output value of the downstream air-fuel ratio sensor 66 when "the additive agent (the urea-water) is not supplied". The output value AFD obtained at step 1260 is referred to as "an output value for a downstream side correction", for convenience.

Figure 14:
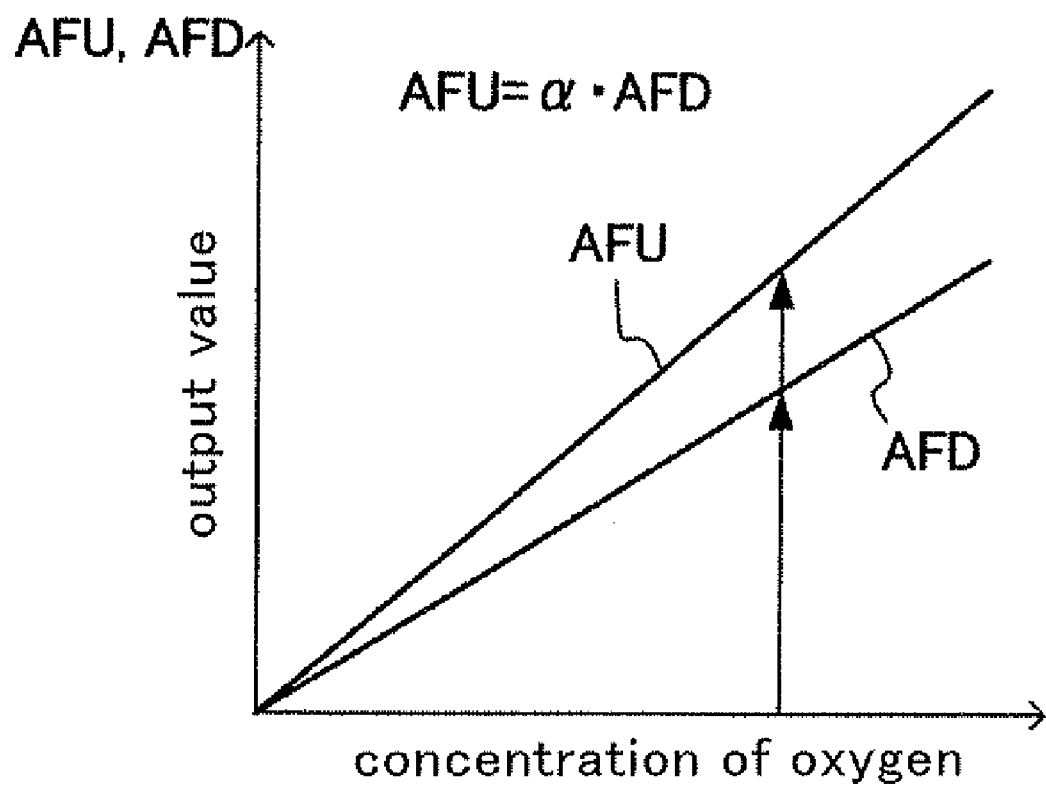
FIG. 14 is a graph showing a relationship between a concentration of oxygen and the output value of the upstream air-fuel ratio sensor, and a relationship between a concentration of oxygen and the output value of the downstream air-fuel ratio sensor.

Step 1270: The CPU calculates the correction coefficient α (=AFU/AFD) by dividing "the obtained output value AFU (the output value for an upstream side correction)" by "the obtained output value AFD (the output value for an downstream side correction)", (see FIG. 14).

Step 1280: The CPU sets the value of the flag XCR at "0".

Step 1290: The CPU stores an initial value Aint into the urea-water supply amount A. The initial value Aint may be constant or a value which varies depending on an estimated amount of nitrogen oxides obtained by multiplying "the intake air amount Ga" by "the concentration DNOx of the nitrogen oxides detected by the NOx sensor 63". That is, the initial value Aint may be set to "a urea-water amount" which can produce an amount of "ammonia" required to reduce "the nitrogen oxides of the estimated amount".

Meanwhile, output values of air-fuel ratio sensors, such as the output value of the upstream air-fuel ratio sensor 64 and the output value of the downstream air-fuel ratio sensor 66, may vary depending upon "individual deviations of output characteristic and their temperatures". Accordingly, even when the ammonia does not flow our from the SCR catalyst 44, the output value of the downstream air-fuel ratio sensor 66 is not necessary equal to the output value of the upstream air-fuel ratio sensor 64. Thus, when the "the ammonia-amount-relating-value $DNH_3$" is simply obtained based on the difference ΔAF between "the output value AFU obtained from the upstream air-fuel ratio sensor 64" and "the output value AFD obtained from the downstream air-fuel ratio sensor 66", there may be a possibility that the ammonia-amount-relating-value is not accurate.

In view of the above, the present exhaust purifying apparatus corrects "the output value AFD while the urea-water is supplied" with using the aforementioned correction coefficient α. This allows the difference in the output characteristic (and including activation level of the sensors) between the upstream air-fuel ratio sensor 64 and the downstream air-fuel ratio sensor 66 to hardly affect on the difference ΔAF. That is, it can be avoided that the difference ΔAF becomes inaccurate with respect to the concentration of ammonia. Accordingly, it is possible to obtain the ammonia-amount-relating-value (the concentration of ammonia) more accurately. Based on the above view, the CPU performs processings steps following step 1320 in FIG. 13.

Specifically, when the CPU starts processing the routine shown in FIG. 13 from step 1300 after the value of the flag XCR is returned to be "0" at step 1280 in FIG. 12, the CPU makes a determination of "Yes" at step 1310 to perform processings of step 1320 to step 1350 in sequence.

Step 1320: The CPU obtains the output value AFU of the upstream air-fuel ratio sensor 64. The exhaust gas which has reached the upstream air-fuel ratio sensor 64 is "the exhaust gas in the state where the nitrogen oxides contained in the exhaust gas has not been purified by the SCR catalyst 44". Accordingly, the output value AFU is a value which varies depending on the concentration of oxygen of such exhaust gas. That is, the output value AFU obtained at step 1320 is a value corresponding to the aforementioned reference value AFDstd and the aforementioned first output value AF1.

Step 1330: The CPU obtains the output value AFD of the downstream air-fuel ratio sensor 66. At this point of time, the urea-water is not injected. However, when the value of the flag XCR is "0", the urea-water is injected at step 1080 described later. In that case, the exhaust gas which passes through the SCR catalyst 44 while the urea-water is being supplied reaches the downstream air-fuel ratio sensor 66. Accordingly, a value based on the output value AFD obtained at step 1330 can be "the aforementioned second output value" (see step 1340 described below).

Step 1340: The CPU multiplies "the obtained output value AFD" by the correction coefficient α to thereby calculate "a correction completed output value AFDc (=α·AFD)" (see FIG. 14). The correction completed output value (the post-corrected value) AFDc corresponds to the second output value. As described above, the correction coefficient α is a value based on the output value for an upstream side correction and the output value for an downstream side correction. Accordingly, it can be said that the output value AFD is corrected based on "the output value for an upstream side correction and the output value for an downstream side correction" at step 1340.

Step 1350: The CPU calculates a difference ΔAF (=AFU−AFDc) between "the obtained output value AFU (the first output value AF1)" and "the obtained correction completed output value AFDc (the second output value AF2)". As is apparent from the reasons described above, the difference ΔAF does not include an error due to the difference in output characteristic between the upstream air-fuel ratio sensor 64 and the downstream air-fuel ratio sensor 66, or the difference ΔAF is a value which includes such error which is extremely small.

Subsequently, the CPU proceeds to step 1360 at which the CPU determines whether or not the difference ΔAF is greater than "0". When the difference ΔAF is greater than "0", the CPU makes a determination of "Yes" at step 1360 to proceed to step 1050 at which the CPU obtains "the concentration of ammonia $DNH_3$" by applying the difference ΔAF to the table MapDNH3(ΔAF).

Subsequently, the CPU proceeds to step 1060 at which the CPU stores, as "an updated urea-water supply amount A", a value obtained by subtracting "a product of the concentration of ammonia $DNH_3$ and the coefficient k" from "the urea-water supply amount A at the present".

Subsequently, the CPU proceeds to step 1070 at which the CPU sets the urea-water injection amount URInj at the urea-water supply amount A. Thereafter, the CPU proceeds to step 1080 to send the instruction signal to the urea-water injector 55 so that the urea-water of the urea-water injection amount URInj is injected from the urea-water injector 55. Then, the CPU proceeds to step 1395 to end the present routine tentatively.

Meanwhile, if the difference ΔAF is less than or equal to "0" when the CPU processes step 1360, the CPU makes a determination of "No" at step 1360 to proceed to step 1090 at which the CPU stores, as "the updated urea-water supply amount A", a value obtained by adding "the constant small positive value Δa" to "the urea-water supply amount A at the present". Subsequently, the CPU performs processings of step 1070 and step 1080. As a result, when the ammonia slip is not occurring, the urea-water supply amount is gradually increased every time the routine shown in FIG. 13 is executed.

It should be noted that, when the CPU makes a determination of "No" at step 1210 in FIG. 12, the CPU proceeds to step 1292 at which the CPU determines "whether or not the value of the correction coefficient updating flag XCR is "1". If the value of the correction coefficient updating flag XCR is "1", the CPU makes a determination of "Yes" at step 1929 to proceed to step 1240. To the contrary, if the value of the correction coefficient updating flag XCR is not "1", the CPU makes a determination of "No" at step 1929 to directly proceed to step 1295 so as to end the routine shown in FIG. 12 tentatively.

As described above, the third exhaust purifying apparatus comprises first output value obtaining means, second output value obtaining means, and additive agent amount control means, etc.

The first output value obtaining means is configured so as to obtain the output value of the upstream air-fuel ratio sensor AFU as the first output value AF1 (See step 1320 in FIG. 13).

The second output value obtaining means is configured so as to obtain "the output value for a downstream side correction" which is "the output value AFD of the downstream air-fuel ratio sensor 66" at the given timing at which "the additive agent is not supplied (is not being supplied)" (See step 1260). Further, the second output value obtaining means is configured so as to obtain "the output value for an upstream side correction" which is "the output value AFU of the upstream air-fuel ratio sensor 64" at "the given timing at which the additive agent is not supplied (is not being supplied)" (See step 1250 in FIG. 12).

Furthermore, the second output value obtaining means corrects "the output value AFD of the downstream air-fuel ratio sensor" when "the additive agent supplying means supplies (is supplying) the additive agent", based on (with using/by) "the correction coefficient α which is determined based on the output value for an upstream side correction and the output value for an downstream side correction", and obtains the corrected value (the correction completed output value AFDc) as "the second output value AF2" (See step 1270 in FIG. 12, and "step 1330 and step 1340" in FIG. 13). Thereafter, the ammonia-amount-relating-value is obtained based on the difference ΔAF between the thus obtained first output value AF1 and the thus obtained second output value AF2 (See step 1360 and step 1050, etc.).

In addition, the additive agent amount control means is configured so as to send "the instruction to stop supplying the additive agent" to the additive agent supplying means (See "step 1220 and 1230" in FIG. 12), in order to make the second output value obtaining means obtain "the output value for an upstream side correction (See step 1250) and the output value for an downstream side correction (See step 1260)", when the second predetermined condition (the correction coefficient updating condition) is satisfied (See step 1210).

As a result, the correction completed output value AFDc which is "the second output value AF2" when the urea-water is being supplied becomes a value which is obtained by the downstream air-fuel ratio sensor 66 as if which has the same output characteristic as the upstream air-fuel ratio sensor 64. Thus, the difference in output characteristic between the upstream air-fuel ratio sensor 64 and the downstream air-fuel ratio sensor 66 is compensated. Accordingly, it is possible to avoid degrading accuracy of "the ammonia-amount-relating-value" which is obtained based on the first output value AF1 and the second output value AF2 (i.e., based on the difference ΔAF between these two values).

Fourth Embodiment

Next, an exhaust purifying apparatus for the internal combustion engine (hereinafter, simply referred to as "a fourth exhaust purifying apparatus") according to a fourth embodiment of the present invention will be described. The fourth exhaust purifying apparatus obtains the ammonia-amount-relating-value, using the output value AFU of the upstream air-fuel ratio sensor 64 and the output value AFD of the downstream air-fuel ratio sensor 66, similarly to the third exhaust purifying apparatus. However, the fourth exhaust purifying apparatus compensates for the difference in output characteristic between the upstream air-fuel ratio sensor 64 and the downstream air-fuel ratio sensor 66 with using a correction coefficient which is different from the correction coefficient α that the third exhaust purifying apparatus uses.

Figure 15:
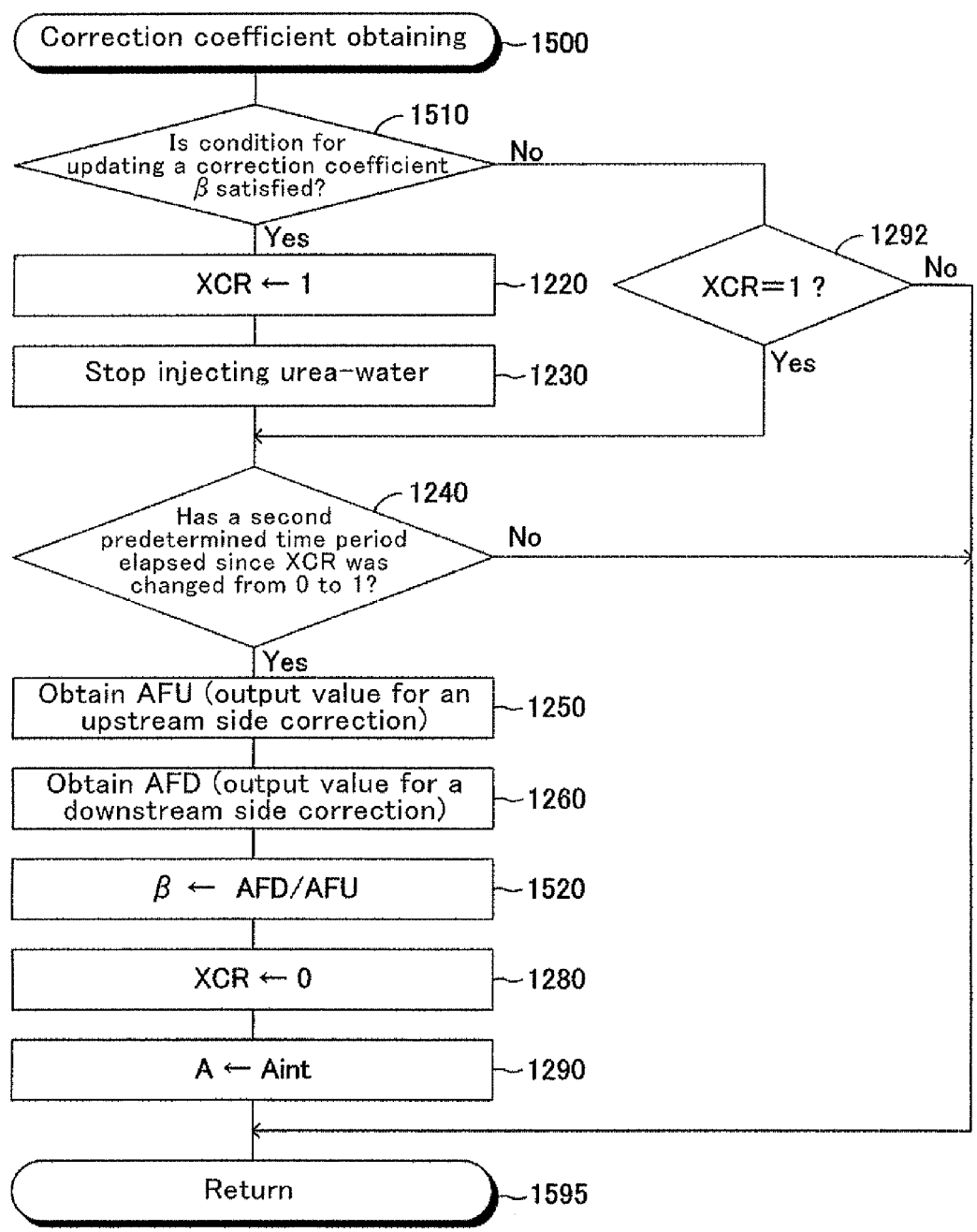
FIG. 15 is a flowchart showing a program executed by a CPU of an exhaust purifying apparatus according to a fourth embodiment of the present invention (a fourth exhaust purifying apparatus)
Figure 16:
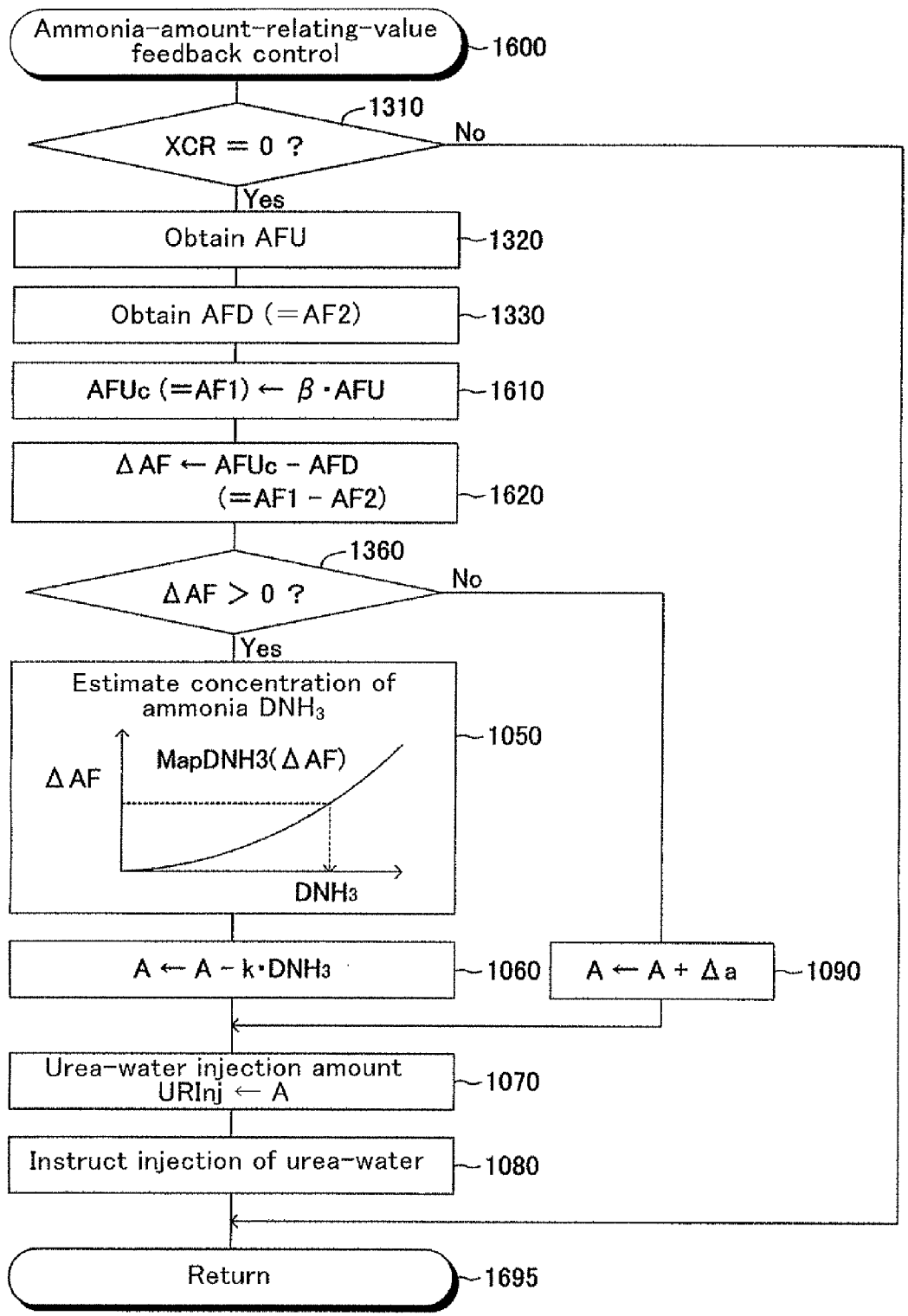
FIG. 16 is a flowchart showing a program executed by the CPU of the fourth exhaust purifying apparatus.

The fourth exhaust purifying apparatus differs from the first exhaust purifying apparatus in that the CPU of the electric controller 70 executes "routines shown as flowcharts in "FIGS. 15 and 16" in place of "FIGS. 9 and 10". Accordingly, the following description specially focuses on this point of difference. It should be noted that each step shown in both FIGS. 15 and 16 at which the same processing is performed as each step which has been described with referring to the other drawings is given the same numeral as one given to such step. Detail descriptions for these steps may be omitted appropriately.

The CPU is configured so as to repeatedly execute "a correction coefficient obtaining routine" shown in FIG. 15 every elapse of a predetermined time. The routine shown in FIG. 15 differs from the routine shown in FIG. 12 in that the "step 1210 and step 1270 in FIG. 12" is replaced by "step 1510 and step 1520 in FIG. 15", respectively. Accordingly, the following description specially focuses on these points of differences.

The CPU determines whether or not a condition for updating (renewing) a correction coefficient β (a correction coefficient updating condition) is satisfied at step 1510. The correction coefficient updating condition is referred to as "a third predetermined condition" for convenience. The correction coefficient updating condition in the present example is that a predetermined constant time period has elapsed since a timing at which the correction coefficient β was previously updated. It should be noted that the correction coefficient updating condition is not limited to the above, but may be a condition similar to the aforementioned first predetermined condition, the aforementioned second predetermined condition, or may be another conditions (e.g., a condition which is satisfied by determining whether or not the both the upstream air-fuel ratio sensor 64 and the downstream air-fuel ratio sensor 66 are activated for the first time after a start of the engine).

Here, it is assumed that the correction coefficient updating condition is satisfied. In this case, the CPU makes a determination of "Yes" at step 1510 to proceed to step 1220 at which the CPU sets the value of correction coefficient updating flag XCR at "1". Further, the CPU stops injecting (supplying) the urea-water at step 1230.

Subsequently, the CPU proceeds to step 1240 at which the CPU determines whether or not the second predetermined time period has elapsed since the flag changing timing. When the second predetermined time period has elapsed since the flag changing timing, the CPU makes a determination of "Yes" at step 1240 which follows "step 1210 to step 1230" and obtains "the output value AFU of the upstream air-fuel ratio sensor 64" as "the output value for an upstream side correction" (step 1250). Further, the CPU obtains "the output value AFD of the downstream air-fuel ratio sensor 66" as "the output value for a downstream side correction" (step 1260).

Subsequently, the CPU proceeds to step 1520 at which the CPU calculates a correction coefficient β (=AFD/AFU=1/α) by dividing "the output value AFD (the output value for a downstream side correction)" by "the obtained output value AFU (the output value for an upstream side correction)". Thereafter, the CPU sets the value of the flag XCR at "0" (step

1280), and sets the urea-water supply amount A at the initial value Aint (step 1290), then ends the present routine tentatively.

The present exhaust purifying apparatus corrects "the output value AFU while the urea-water is not being supplied" with the correction coefficient β. This allows the difference in the output characteristic (and including activation level of the sensors) between the upstream air-fuel ratio sensor 64 and the downstream air-fuel ratio sensor 66 to hardly affect on the difference ΔAF.

That is, the CPU obtains "the output value AFU of the upstream air-fuel ratio sensor 64" at step 1320 which follows step 1310 in FIG. 16, and obtains "the output value AFD of the downstream air-fuel ratio sensor 66" as the second output value AF2 at step 1330.

Subsequently, at step 1610, the CPU multiplies "the obtained output value AFU" by the correction coefficient β to thereby calculate a correction completed output value AFUc (=β·AFU). The correction completed output value (the post-corrected value) AFUc corresponds to the first output value AF1. The correction coefficient 3 is a value based on the output value for an upstream side correction and the output value for an downstream side correction. Accordingly, it can be said that the output value AFU is corrected based on "the output value for an upstream side correction and the output value for an downstream side correction" at step 1610.

The CPU calculates a difference ΔAF (=AFUc−AFD) between "the obtained correction completed output value AFUc (the first output value AF1)" and "the obtained output value AFD (the second output value AF2)". As is apparent from the reasons described above, the difference ΔAF does not include an error due to the difference in output characteristic between the upstream air-fuel ratio sensor 64 and the downstream air-fuel ratio sensor 66, or the difference ΔAF is a value which includes such error which is extremely small.

Subsequently, the CPU proceeds to steps which follows step 1360. Thus, if the difference ΔAF is greater than "0", the CPU obtains "the concentration of ammonia $DNH_3$" (step 1050), determines the urea-water supply amount A (the urea-water injection amount URInj), and sends the instruction signal to the urea-water injector 55 so that the urea-water of the urea-water injection amount URInj is injected from the urea-water injector 55 (step 1060 to step 1080). Thereafter, the CPU proceeds to step 1695 to end the present routine tentatively. On the other hand, if the difference ΔAF is less than or equal to "0", the CPU increases the urea-water supply amount A by the predetermined amount Δa (step 1090), and sends the instruction signal to the urea-water injector 55 so that the urea-water of the increased urea-water injection amount URInj is injected from the urea-water injector 55 (step 1070 to step 1080).

As described above, the fourth exhaust purifying apparatus comprises first output value obtaining means, second output value obtaining means, and additive agent amount control means, etc.

The second output value obtaining means obtains "the output value AFD of the downstream air-fuel ratio sensor" when "the additive agent supplying means supplies (is supplying) the additive agent", "as the second output value" (step 1330 in FIG. 16).

Meanwhile, the first output value obtaining means obtains "the output value for a upstream side correction" which is "the output value AFU of the upstream air-fuel ratio sensor 64" at "the given timing at which the additive agent is not supplied" (step 1250 in FIG. 15). Furthermore, the first output value obtaining means obtains "the output value for a downstream side correction" which is "the output value AFD of the downstream air-fuel ratio sensor 66" at "the given timing at which the additive agent is not supplied" (step 1260 in FIG. 15).

Furthermore, the first output value obtaining means corrects "the output value AFU of the upstream air-fuel ratio sensor 64" when "the additive agent supplying means supplies (is supplying) the additive agent", based on (with using/by) "the correction coefficient β which is determined based on the output value for an upstream side correction and the output value for an downstream side correction", and obtains the corrected value (the correction completed output value AFUc) as "the first output value AF1" (See step 1610 in FIG. 16). Thereafter, the ammonia-amount-relating-value is obtained based on the difference ΔAF between the thus obtained first output value and the thus obtained second output value (See step "1360 and step 1050" in FIG. 16, etc.).

In addition, the additive agent amount control means is configured so as to send "the instruction to stop supplying the additive agent" to the additive agent supplying means (See "step 1220 and 1230" in FIG. 15), in order to make the first output value obtaining means obtain "the output value for an upstream side correction (See step 1250 in FIG. 15) and the output value for an downstream side correction (See step 1260 in FIG. 15)", when the third predetermined condition (the correction coefficient updating condition) is satisfied (See step 1510 in FIG. 15).

As a result, the correction completed output value AFUc which is "the first output value AF1" when the urea-water is being supplied becomes a value which is obtained by the upstream air-fuel ratio sensor 64 as if which has the same output characteristic as the downstream air-fuel ratio sensor 66. Thus, the difference in output characteristic between the upstream air-fuel ratio sensor 64 and the downstream air-fuel ratio sensor 66 is compensated. Accordingly, it is possible to avoid degrading accuracy of "the ammonia-amount-relating-value" which is obtained based on the first output value AF1 and the second output value AF2 (i.e., based on the difference ΔAF between these two values).

<First Modification of the Downstream Air-Fuel Ratio Sensor>

Next will be described a first modified downstream air-fuel ratio sensor 66 used in the embodiments according to the present invention. As described, the downstream air-fuel ratio sensor 66 is configured in such a manner that it outputs the output value AFD which varies in accordance with "the concentration (or the partial pressure) of oxygen at the exhaust gas side electrode layer 66b" of "a gas which has reached the exhaust gas side electrode layer 66b after passing through the diffusion resistance layer 66d". Further, when the downstream gas to be detected contains oxygen and ammonia, "the ammonia whose diffusion speed is high" reaches the exhaust gas side electrode layer 66b more preferentially than "the oxygen whose diffusion speed is low". It should be noted that, in typical air-fuel ratio sensor (e.g., the upstream air-fuel ratio sensor 64), a diameter of each fine pores of the diffusion resistance layer 66d is adjusted so as to be "a diameter (XO2) which allows the oxygen molecules to easily pass through the diffusion resistance layer 66d", as shown by a dash line L1 in FIG. 17.

Figure 17:
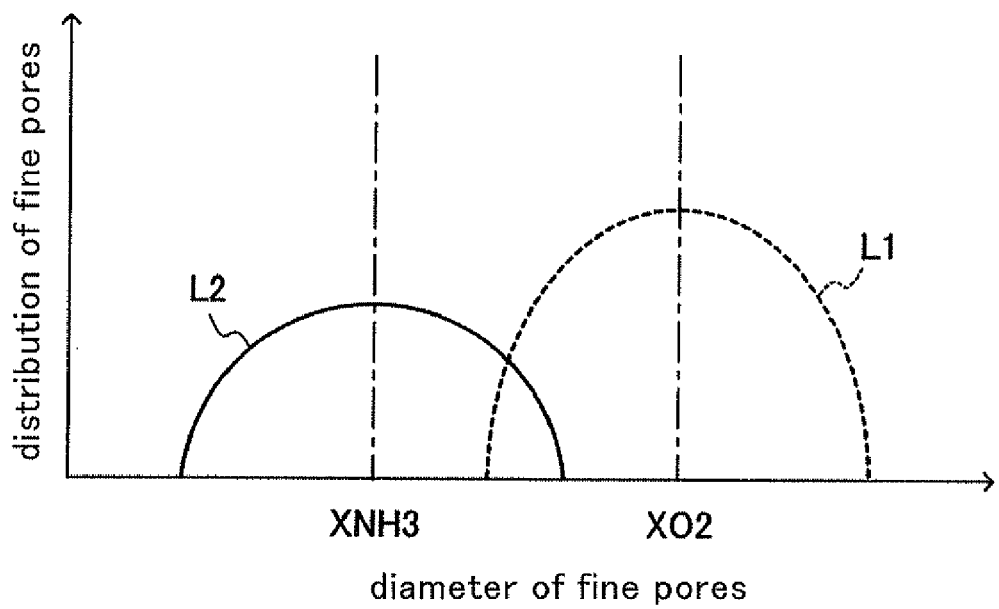
FIG. 17 is a graph showing a distribution of a diameter of fine pores in a diffusion resistance layer of the upstream air-fuel ratio sensor (and of the downstream air-fuel ratio sensor which the first exhaust purifying apparatus adopts), and a distribution of a diameter of fine pores in a diffusion resistance layer of a downstream air-fuel ratio sensor according to a first modification.

To the contrary, the first modified downstream air-fuel ratio sensor 66 is adjusted/configured in such a manner that a diameter of each fine pores of the diffusion resistance layer 66d is adjusted so as to be "a diameter (XNH3) which allows the ammonia molecules to easily pass through the diffusion resistance layer 66d", as shown by a solid line L2 in FIG. 17. Here, the XO2>XNH3.

As described, the diffusion resistance layer (diffusion controlling layer) is the porous layer having "ceramic grains" and "fine pores formed between or among the ceramic grains". Thus, molecules of gas (such as oxygen molecules and ammonia molecules) pass through the fine pores with or while colliding with the ceramic grains. Therefore, if the diameter of the fine pores of the diffusion resistance layer is adjusted so as to be "a diameter (XNH3) which allows the ammonia molecules to easily pass through the diffusion resistance layer, the mean diffusion distance of oxygen molecules becomes much greater than the mean diffusion distance of ammonia molecules. As a result, the first modified downstream air-fuel ratio sensor is a sensor which is more sensitive to ammonia, compared with the upstream air-fuel ratio sensor 64 and the downstream air-fuel ratio sensor 66.

Figure 18:
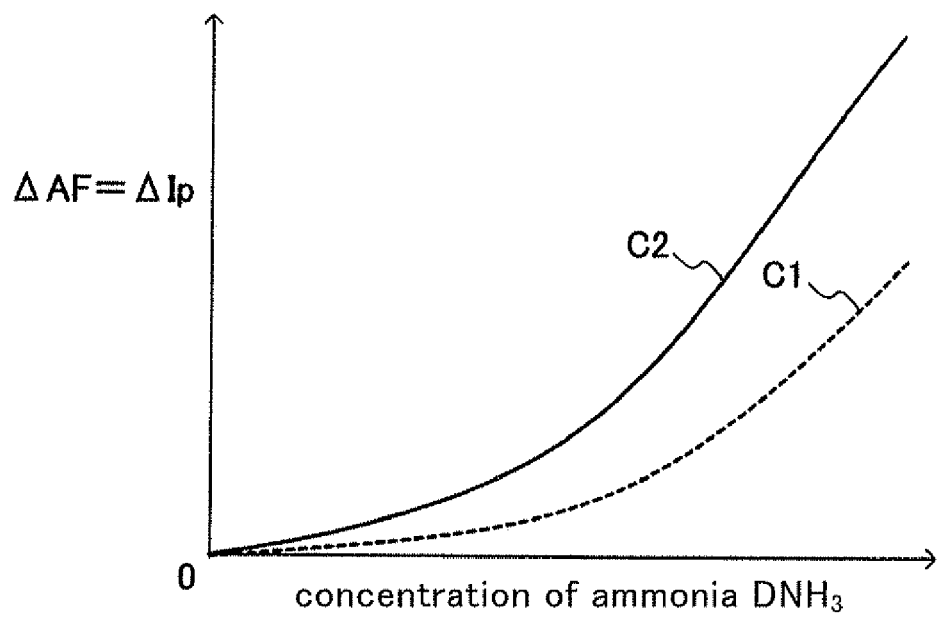
FIG. 18 is a graph showing "a relationship between a variation (decreasing) amount in the output of the upstream air-fuel ratio sensor (and of the downstream air-fuel ratio sensor which the first exhaust purifying apparatus adopts) and a concentration of ammonia", and "a relationship between a variation (decreasing) amount in the output of the downstream air-fuel ratio sensor according to the first modification and a concentration of ammonia"

In FIG. 18, the broken line C1 shows characteristic of a downstream air-fuel ratio sensor having a diffusion resistance layer which is the same as the diffusion resistance layer of the upstream air-fuel ratio sensor 64 (i.e., an air-fuel ratio sensor having a diffusion resistance layer which is configured in such a manner that a diameter of fine pores of the diffusion resistance layer 66d is adjusted so as to be "a diameter (XO2) which allows the oxygen molecules to easily pass through the diffusion resistance layer", whereas, the solid line C2 shows characteristic of the first modified downstream air-fuel ratio sensor. As is apparent from FIG. 18, the first modified downstream air-fuel ratio sensor can provide "the above described difference $\Delta AF$" which is greater than the difference $\Delta AF$ which the upstream air-fuel ratio sensor 64 provides, for the arbitrary concentration of ammonia.

In other words, the first modified downstream air-fuel ratio sensor is more sensitive to ammonia than the upstream air-fuel ratio sensor 64 and the downstream air-fuel ratio sensor 66. Accordingly, the exhaust purifying apparatuses according to the embodiments described above can obtain "the ammonia-amount-relating-value" which is more accurate by use of such first modified downstream air-fuel ratio sensor.

<Second Modification of the Downstream Air-Fuel Ratio Sensor>

Next will be described a second modification 68 of the downstream air-fuel ratio sensor 66 with referring to FIG. 19. The second modified downstream air-fuel ratio sensor 68 differs from the downstream air-fuel ratio sensor 66 in that the diffusion resistance layer 66d of the downstream air-fuel ratio sensor 66 is replaced by a diffusion resistance layer 68d of the downstream air-fuel ratio sensor 68. Accordingly, the following description specially focuses on this point of difference.

Figure 19:
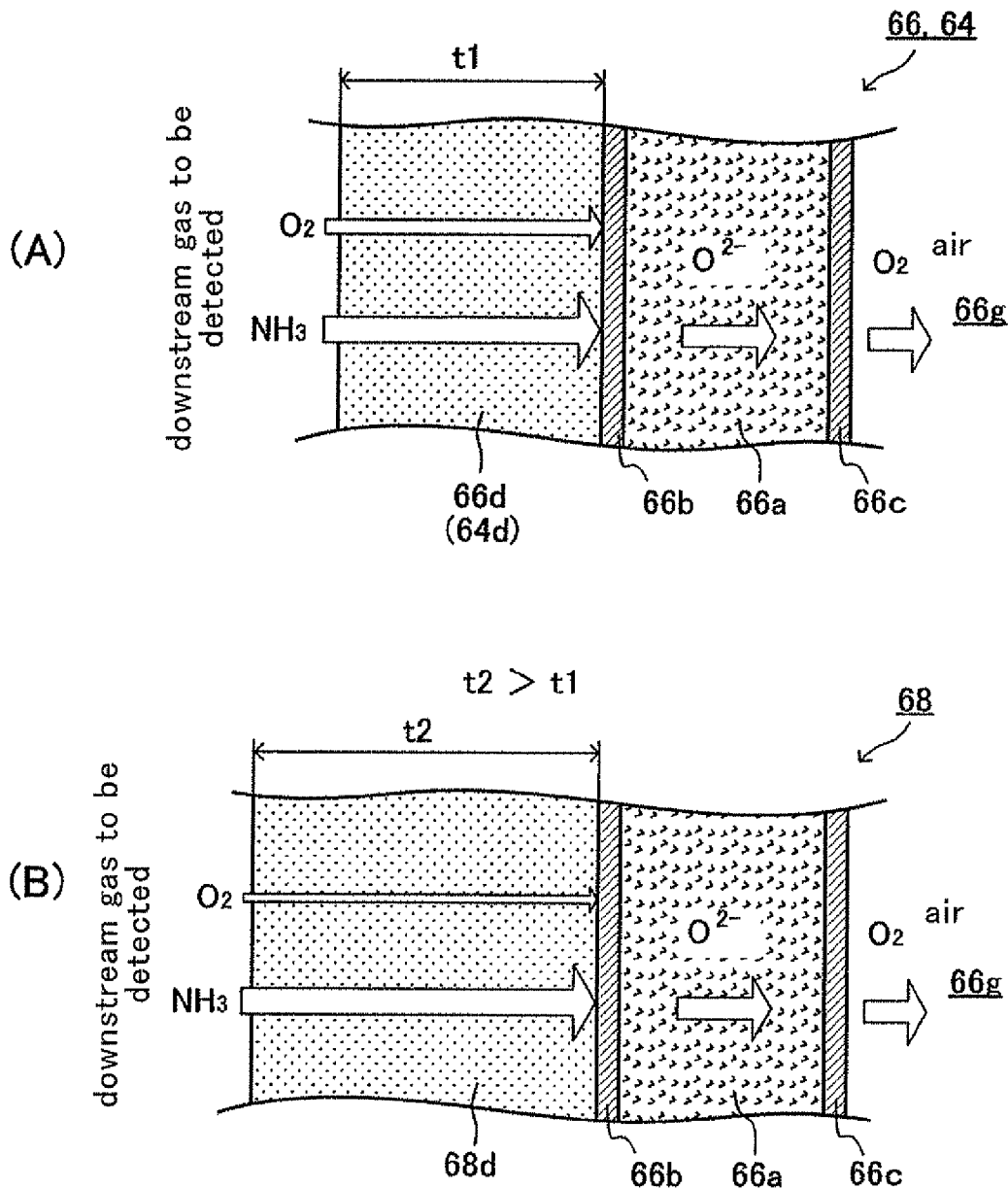
FIG. 19 includes (A) and (B), where (A) is a partial cross sectional view of a typical air-fuel ratio sensor (the upstream air-fuel ratio sensor in the present example and the downstream air-fuel ratio sensor which the first exhaust purifying apparatus adopts), and (B) is a partial cross sectional view of a downstream air-fuel ratio sensor according to a second modification.

(A) of FIG. 19 shows a partial cross sectional view of the downstream air-fuel ratio sensor 66 and the upstream air-fuel ratio sensor 64. (B) of FIG. 19 shows a partial cross sectional view of the downstream air-fuel ratio sensor 68. It can be understood form (A) and (B) of FIG. 19, a thickness t2 of the diffusion resistance layer 68d is greater than a thickness t1 of the diffusion resistance layer 66d (or 64d).

By means of such structure of the sensor 68, a difference between the mean diffusion distance of oxygen molecule and the mean diffusion distance of ammonia molecule becomes much greater. As a result, the second modified downstream air-fuel ratio sensor 68 is more sensitive to ammonia, compared with the upstream air-fuel ratio sensor 64 and the downstream air-fuel ratio sensor 66. Accordingly, the exhaust purifying apparatuses according to the embodiments described above can obtain "the ammonia-amount-relating-value" which is more accurate by use of such second modified downstream air-fuel ratio sensor 68.

It should be noted that each of the exhaust purifying apparatuses of the present invention can adopt a downstream air-fuel ratio sensor which is configured by combining the feature of "adjusting the diameter of fine pores of the diffusion resistance layer for a diameter of an ammonia molecule" and the feature of "thickening the diffusion resistance layer". This allows the downstream air-fuel ratio sensor to be much more sensitive to ammonia. Thus, the exhaust purifying apparatus can obtain "the ammonia-amount-relating-value" which is much more accurate.

It is preferable that, in a case where the upstream air-fuel ratio sensor 64 and the downstream air-fuel ratio sensor whose diffusion resistance layer is different from the diffusion resistance layer of the upstream air-fuel ratio sensor 64 are used, either one of "the first, the third, and the fourth exhaust purifying apparatuses" be adopted.

It can be said that the above described first and second modified downstream air-fuel ratio sensors have the following features by defining the distance L1 to L4 as described below.

The first diffusion distance L1 is a sum of distance (mean moving distance) which the ammonia molecule needs to travel (or takes) when it moves from the outer surface of the diffusion resistance layer to the exhaust gas side electrode layer while passing through the diffusion resistance layer in either one of the first and second modified downstream air-fuel ratio sensors.

The second diffusion distance L2 is a sum of distance (mean moving distance) which the oxygen molecule needs to travel (or takes) when it moves from the outer surface of the diffusion resistance layer to the exhaust gas side electrode layer while passing through the diffusion resistance layer in either one of the first and second modified downstream air-fuel ratio sensors.

The third diffusion distance L3 is a sum of distance (mean moving distance) which the ammonia molecule needs to travel (or takes) when it moves from the outer surface of the diffusion resistance layer to the exhaust gas side electrode layer while passing through the diffusion resistance layer in the upstream air-fuel ratio sensor 64.

The fourth diffusion distance L4 is a sum of distance (mean moving distance) which the oxygen molecule needs to travel (or takes) when it moves from the outer surface of the diffusion resistance layer to the exhaust gas side electrode layer while passing through the diffusion resistance layer in the upstream air-fuel ratio sensor 64.

Each of the first and second modified downstream air-fuel ratio sensors is characterized in that a ratio (L2/L1) of the second diffusion distance L2 to the first diffusion distance L1 is greater than a ratio (L4/L3) of the fourth diffusion distance L4 to the third diffusion distance L3.

As described above, each of the embodiments of the exhaust purifying apparatus according to the present invention can obtain the value relating to an amount of ammonia which flows out from the SCR catalyst 44 by using the inexpensive air-fuel ratio sensor without using the expensive NOx sensor. Thus, the inexpensive exhaust purifying apparatus can be provided.

The present invention is not limited to the embodiments described above, various modifications may be adopted without departing from the scope of the invention. For example, the difference $\Delta AF$ may be compared with "a minute positive value $\delta th$" in place of "0" at step 1040 in FIG. 10, step 1140 in FIG. 11, and step 1360 in FIGS. 13 and 16. In this case, if the difference $\Delta AF$ is equal to or more than "0" and is equal to or less than "the value $\delta th$", the CPU may be configured so as not to vary "the urea-water supply amount A".

Furthermore, each of the exhaust purifying apparatuses according to the embodiments described above can be used as an anomaly diagnostic apparatus of the SCR catalyst 44. In this case, each of the exhaust purifying apparatuses supplies a predetermined amount of the urea-water from the injector 55 when an operating condition is in a predetermined condition. Meanwhile, the exhaust purifying apparatus stores in the ROM "a concentration of ammonia which is inferred with respect to the predetermine amount of the urea-water" when the SCR catalyst 44 is normal, as "a threshold of concentration of ammonia". Then, the exhaust purifying apparatus is configured in such a manner that it determines that the SCR catalyst 44 is in an anomalous state, when the concentration of ammonia obtained by the exhaust purifying apparatuses according to the embodiments is greater than the threshold of concentration of ammonia by a predetermined value.

The invention claimed is:

1. An exhaust purifying apparatus for an internal combustion engine comprising:
   a SCR catalyst, which is disposed in an exhaust passage of said engine and purifies nitrogen oxides contained in an exhaust gas discharged from said engine by reducing said nitrogen oxides by ammonia;
   a downstream air-fuel ratio sensor, disposed at a position downstream of said SCR catalyst in said exhaust passage and including a solid electrolyte layer, an exhaust gas side electrode layer, an atmospheric air side electrode layer exposed in a space to which atmosphere is introduced, and a diffusion resistance layer, in which said exhaust gas side electrode layer and said atmospheric air side electrode layer are formed on both surfaces of said solid electrolyte layer so as to oppose to each other to sandwich said solid electrolyte layer, and in which said exhaust gas side electrode layer is covered by said diffusion resistance layer, said downstream air-fuel ratio sensor outputting an output value varying in accordance with a concentration of oxygen at said exhaust gas side electrode layer of a gas which reaches said exhaust gas side electrode layer after passing through said diffusion resistance layer;
   additive agent supplying means for supplying an additive agent including urea-water or ammonia at a position upstream of said SCR catalyst in said exhaust passage in response to an instruction; and
   a controller that includes control logic, which when executed:
      obtains a first output value which varies in accordance with a concentration of oxygen of said exhaust gas which is in a state where nitrogen oxides contained in said exhaust gas have not been purified by said SCR catalyst;
      obtains a second output value which is a value based on said output value of said downstream air-fuel ratio sensor when said additive agent supplying means supplies said additive agent;
      obtains an ammonia-amount-relating-value which relates to an amount of ammonia which flows out from said SCR catalyst based on a difference between said first output value and said second output value;
      determines an amount of said additive agent to be supplied based on said ammonia-amount-relating-value, and
      sends to said additive agent supplying means an instruction to supply said determined amount of said additive agent, wherein the controller includes control logic to:
   obtain, as said first output value, said output value of said downstream air-fuel ratio sensor when said additive agent supplying means does not supply said additive agent;
   obtain, as said second output value, said output value of said downstream air-fuel ratio sensor when said additive agent supplying means supplies said additive agent; and
   send to said additive agent supplying means an instruction to stop supplying said additive agent in order to obtain said first output value, when a first predetermined condition is satisfied.

2. An exhaust purifying apparatus for an internal combustion engine comprising:
   a SCR catalyst, which is disposed in an exhaust passage of said engine and purifies nitrogen oxides contained in an exhaust gas discharged from said engine by reducing said nitrogen oxides by ammonia;
   a downstream air-fuel ratio sensor, disposed at a position downstream of said SCR catalyst in said exhaust passage and including a solid electrolyte layer, an exhaust gas side electrode layer, an atmospheric air side electrode layer exposed in a space to which atmosphere is introduced, and a diffusion resistance layer, in which said exhaust gas side electrode layer and said atmospheric air side electrode layer are formed on both surfaces of said solid electrolyte layer so as to oppose to each other to sandwich said solid electrolyte layer, and in which said exhaust gas side electrode layer is covered by said diffusion resistance layer, said downstream air-fuel ratio sensor outputting an output value varying in accordance with a concentration of oxygen at said exhaust gas side electrode layer of a gas which reaches said exhaust gas side electrode layer after passing through said diffusion resistance layer;
   an upstream air-fuel ratio sensor which is disposed at a position upstream of said SCR catalyst in said exhaust passage and includes a solid electrolyte layer, an exhaust gas side electrode layer, an atmospheric air side electrode layer exposed in a space to which atmosphere is introduced, and a diffusion resistance layer, in which said exhaust gas side electrode layer and said atmospheric air side electrode layer are formed on both surfaces of said solid electrolyte layer so as to oppose to each other to sandwich said solid electrolyte layer, and in which said exhaust gas side electrode layer is covered by said diffusion resistance layer, said upstream air-fuel ratio sensor outputting an output value varying in accordance with a concentration of oxygen at said exhaust gas side electrode layer of a gas which reaches said exhaust gas side electrode layer after passing through said diffusion resistance layer;
   additive agent supplying means for supplying an additive agent including urea-water or ammonia at a position upstream of said SCR catalyst in said exhaust passage in response to an instruction; and
   a controller that includes control logic, which when executed:
      obtains a first output value which varies in accordance with a concentration of oxygen of said exhaust gas which is in a state where nitrogen oxides contained in said exhaust gas have not been purified by said SCR catalyst;

obtains a second output value which is a value based on said output value of said downstream air-fuel ratio sensor when said additive agent supplying means supplies said additive agent;

obtains an ammonia-amount-relating-value which relates to an amount of ammonia which flows out from said SCR catalyst based on a difference between said first output value and said second output value;

determines an amount of said additive agent to be supplied based on said ammonia-amount-relating-value; and sends to said additive agent supplying means an instruction to supply said determined amount of said additive agent, wherein the controller includes control logic to:
obtain, as said first output value, said output value of said upstream air-fuel ratio sensor;
obtain an output value for an upstream side correction which is said output value of said upstream air-fuel ratio sensor at a given timing at which said additive agent supplying means does not supply said additive agent, obtain an output value for an downstream side correction which is said output value of said downstream air-fuel ratio sensor at said given timing, and correct, based on said output value for an upstream side correction and said output value for an downstream side correction, said output value of said downstream air-fuel ratio sensor when said additive agent supplying means supplies said additive agent in order to obtain a corrected value as said second output value; and
send to said additive agent supplying means an instruction to stop supplying said additive agent in order to obtain said output value for an upstream side correction and said output value for an downstream side correction, when a second predetermined condition is satisfied.

3. The exhaust purifying apparatus for an internal combustion engine according to claim 2, wherein:
a ratio of a second diffusion distance to a first diffusion distance is greater than a ratio of a fourth diffusion distance to a third diffusion distance, wherein,
said first diffusion distance is defined to be a sum of distance which the ammonia molecule needs when it moves from an outer surface of said diffusion resistance layer to said exhaust gas side electrode layer while passing through said diffusion resistance layer in said downstream air-fuel ratio sensor,
said second diffusion distance is a sum of distance which the oxygen molecule needs when it moves from said outer surface of said diffusion resistance layer to said exhaust gas side electrode layer while passing through said diffusion resistance layer in said downstream air-fuel ratio sensor,
said third diffusion distance is defined to be a sum of distance which the ammonia molecule needs when it moves from said outer surface of said diffusion resistance layer to said exhaust gas side electrode layer while passing through said diffusion resistance layer in said upstream air-fuel ratio sensor, and
said fourth diffusion distance is defined to be a sum of distance which the oxygen molecule needs when it moves from said outer surface of the diffusion resistance layer to said exhaust gas side electrode layer while passing through said diffusion resistance layer in said upstream air-fuel ratio sensor.

4. An exhaust purifying apparatus for an internal combustion engine comprising:
a SCR catalyst, which is disposed in an exhaust passage of said engine and purifies nitrogen oxides contained in an exhaust gas discharged from said engine by reducing said nitrogen oxides by ammonia;
a downstream air-fuel ratio sensor, disposed at a position downstream of said SCR catalyst in said exhaust passage and including a solid electrolyte layer, an exhaust gas side electrode layer, an atmospheric air side electrode layer exposed in a space to which atmosphere is introduced, and a diffusion resistance layer, in which said exhaust gas side electrode layer and said atmospheric air side electrode layer are formed on both surfaces of said solid electrolyte layer so as to oppose to each other to sandwich said solid electrolyte layer, and in which said exhaust gas side electrode layer is covered by said diffusion resistance layer, said downstream air-fuel ratio sensor outputting an output value varying in accordance with a concentration of oxygen at said exhaust gas side electrode layer of a gas which reaches said exhaust gas side electrode layer after passing through said diffusion resistance layer;
an upstream air-fuel ratio sensor which is disposed at a position upstream of said SCR catalyst in said exhaust passage and includes a solid electrolyte layer, an exhaust gas side electrode layer, an atmospheric air side electrode layer exposed in a space to which atmosphere is introduced, and a diffusion resistance layer, in which said exhaust gas side electrode layer and said atmospheric air side electrode layer are formed on both surfaces of said solid electrolyte layer so as to oppose to each other to sandwich said solid electrolyte layer, and in which said exhaust gas side electrode layer is covered by said diffusion resistance layer, said upstream air-fuel ratio sensor outputting an output value varying in accordance with a concentration of oxygen at said exhaust gas side electrode layer of a gas which reaches said exhaust gas side electrode layer after passing through said diffusion resistance layer;
additive agent supplying means for supplying an additive agent including urea-water or ammonia at a position upstream of said SCR catalyst in said exhaust passage in response to an instruction; and
a controller that includes control logic, which when executed:
obtains a first output value which varies in accordance with a concentration of oxygen of said exhaust gas which is in a state where nitrogen oxides contained in said exhaust gas have not been purified by said SCR catalyst;
obtains a second output value which is a value based on said output value of said downstream air-fuel ratio sensor when said additive agent supplying means supplies said additive agent;
obtains an ammonia-amount-relating-value which relates to an amount of ammonia which flows out from said SCR catalyst based on a difference between said first output value and said second output value;
determines an amount of said additive agent to be supplied based on said ammonia-amount-relating-value; and
sends to said additive agent supplying means an instruction to supply said determined amount of said additive agent, wherein the controller includes control logic to:
obtain, as said second output value, said output value of said downstream air-fuel ratio sensor when said additive agent supplying means supplies said additive agent;
obtain an output value for a upstream side correction which is said output value of said upstream air-fuel ratio sensor at a given timing at which said additive agent supplying means does not supply said additive agent, obtain an output value for a downstream side correction which is said output value of said downstream air-fuel ratio sensor at said given timing, and correct, based on said output value for an upstream side correction and said output value for an downstream side correction, said output value of said upstream air-fuel ratio sensor when said additive agent supplying means supplies said additive agent in order to obtain a corrected value as said first output value; and
send to said additive agent supplying means an instruction to stop supplying said additive agent in order to obtain said output value for an upstream side correction and said output value for an downstream side correction, when a third predetermined condition is satisfied.

5. The exhaust purifying apparatus for an internal combustion engine according to claim 4, wherein:

a ratio of a second diffusion distance to a first diffusion distance is greater than a ratio of a fourth diffusion distance to a third diffusion distance, wherein, said first diffusion distance is defined to be a sum of distance which the ammonia molecule needs when it moves from an outer surface of said diffusion resistance layer to said exhaust gas side electrode layer while passing through said diffusion resistance layer in said downstream air-fuel ratio sensor, said second diffusion distance is a sum of distance which the oxygen molecule needs when it moves from said outer surface of said diffusion resistance layer to said exhaust gas side electrode layer while passing through said diffusion resistance layer in said downstream air-fuel ratio sensor, said third diffusion distance is defined to be a sum of distance which the ammonia molecule needs when it moves from said outer surface of said diffusion resistance layer to said exhaust gas side electrode layer while passing through said diffusion resistance layer in said upstream air-fuel ratio sensor, and said fourth diffusion distance is defined to be a sum of distance which the oxygen molecule needs when it moves from said outer surface of the diffusion resistance layer to said exhaust gas side electrode layer while passing through said diffusion resistance layer in said upstream air-fuel ratio sensor.

* * * * *